(12) United States Patent
Nystedt et al.

(10) Patent No.: US 8,546,353 B2
(45) Date of Patent: Oct. 1, 2013

(54) COMPOUNDS AND COMBINATIONS

(75) Inventors: Johanna Nystedt, Helsinki (FI); Heidi Anderson, Helsinki (FI); Tero Satomaa, Helsinki (FI); Jari Natunen, Vantaa (FI); Jari Helin, Rajamäki (FI); Juhani Saarinen, Helsinki (FI)

(73) Assignee: Glykos Finland Oy (FI)

( * ) Notice: Subject to any disclaimer, the term of this patent is extended or adjusted under 35 U.S.C. 154(b) by 0 days.

(21) Appl. No.: 13/102,451

(22) Filed: May 6, 2011

(65) Prior Publication Data
US 2011/0274646 A1 Nov. 10, 2011

Related U.S. Application Data

(60) Provisional application No. 61/331,888, filed on May 6, 2010.

(51) Int. Cl.
*A61K 31/728* (2006.01)
*C08B 37/00* (2006.01)
*C08L 5/00* (2006.01)
*C08B 37/08* (2006.01)

(52) U.S. Cl.
CPC .......... *A61K 31/728* (2013.01); *C08B 37/0072* (2013.01); *C08L 5/00* (2013.01)
USPC ........................................... 514/55; 536/55.1

(58) Field of Classification Search
None
See application file for complete search history.

(56) References Cited

U.S. PATENT DOCUMENTS

| | | | |
|---|---|---|---|
| 5,008,253 A * | 4/1991 | Casu et al. ................ | 514/54 |
| 6,051,701 A * | 4/2000 | Cialdi et al. ............... | 536/123 |
| 6,579,978 B1 * | 6/2003 | Renier et al. .............. | 536/53 |
| 6,875,753 B1 | 4/2005 | Pilarski | |
| 7,446,100 B2 | 11/2008 | Pilarski | |
| 2004/0204384 A1 | 10/2004 | Smadja-Joffe et al. | |

FOREIGN PATENT DOCUMENTS

| | | |
|---|---|---|
| EP | 1350518 A1 | 10/2003 |
| EP | 2025687 A1 | 2/2009 |
| FR | 2789587 A1 | 8/2000 |
| WO | 2007/137674 A1 | 12/2007 |
| WO | 2008/019371 A1 | 2/2008 |

OTHER PUBLICATIONS

Ludowieg et al., "The Mechanis of Action of Hyaluronidases" The Journal of Biological Chemistry (1961) vol. 236 No. 2 pp. 333-339.*
Kunze et al., "Sulfated hyaluronan derivatives reduce the proliferation rate of primary rat calvarial osteoblasts" Glycoconjugate Journal (2010) vol. 27 pp. 151-158.*
Extended European Search Report relating to corresponding EP Application No. 11165109.7, Jul. 28, 2011.
Crescenzi, et al., "New Cross-Linked and Sulfated Derivatives of Partially Deacetylated Hyaluronan: Synthesis and-Preliminary Characterization," Biopolymers, vol. 64, 86-94 (2002).
Matrosova, et al., "Hyaluronic Acid Facilitates the Recovery of Hematopoiesis Following 5-Fluorouracil Administration," Stem Cells, 2004; 22:544-555.
Meyer, et al., "Sustained in Vivo Activity of Recombinant Human Granulocyte Colony Stimulating Factor (rHG-CSF) Incorporated into Hyaluronan," Journal of Controlled Release, 35 (1995) 67-72.
Suzuki, et al., "Preparation and Inhibitory Activity on Hyaluronidase of O-Sulfated Hyaluro-Oligosaccharides," Glycobiology, vol. 11, No. 1, 57-64, 2001.
West, et al., "Angiogenesis Induced by Degradation Products of Hyaluronic Acid," Science, vol. 228, 1324-1326, (1985).
English Abstract of FR 2789587, (2000).

* cited by examiner

*Primary Examiner* — Eric S Olson
(74) *Attorney, Agent, or Firm* — Banner & Witcoff, Ltd.

(57) ABSTRACT

The present invention relates to a combination of a hyaluronan oligomer and/or polymer and a factor capable of mobilizing stem cells. The present invention also relates to a method for altering the relative amounts of blood cells and/or the types of blood cells in a subject by administering the combination to the subject. Further, the present invention relates to a method for mobilizing stem cells to the bloodstream of a subject by administering the combination to the subject. Additionally, the present invention relates to a hyaluronan oligomer and/or polymer.

21 Claims, 16 Drawing Sheets

COMPOUNDS AND COMBINATIONS

RELATED APPLICATIONS

This application claims priority to U.S. Provisional Patent Application No. 61/331,888, filed on May 6, 2010 and is hereby incorporated herein by reference in its entirety for all purposes.

FIELD OF THE INVENTION

The present invention relates to a combination and/or combined use of a sulphated hyaluronan oligomer and/or polymer and at least one factor capable of releasing stem cells. The present invention also relates to a method for repairing blood count and/or altering the relative amounts of blood cells and/or the types of blood cells in a subject by administering the combination to the subject. Further, the present invention relates to a method for mobilizing stem cells to the bloodstream of a subject by administering the combination to the subject. The present invention additionally relates to a method for repairing blood count and/or altering the relative amounts of blood cells and/or the types of blood cells in a subject by administering a non-sulphated and/or a sulphated hyaluronan oligomer and/or polymer to said subject. The present invention also relates to sulphated and/or non-sulphated hyaluronan oligomers and/or polymers.

BACKGROUND OF THE INVENTION

Mobilization of stem cells into peripheral blood is intensively studied presently. Mobilized, peripheral blood stem cells (PBSC) are increasingly used for both autologous and allogeneic transplants.

Factors and/or agents capable of releasing stem cells from the site of origin, typically bone marrow, are used to mobilize stem cells into circulation and increase their number in peripheral blood, thus allowing a more efficient collection of larger number of stem cells from the circulation. Cytokines, such as, granulocyte-colony-stimulating factor (G-CSF) and granulocyte-macrophage colony-stimulating factor (GM-CSF), and CXCR4-receptor inhibitors, such as, Mozobil™ are examples of factors and/or agents that are capable of mobilizing stem cells into circulating blood of a subject.

Patent application WO 2008/019371 describes a combination of G-CSF with at least one CXCR4 inhibitor and at least one CXCR2 agonist. The combination is used to mobilize progenitor and/or stem cells into the bloodstream of a subject.

U.S. Pat. No. 6,875,753 describes administration of hyaluronic acid having molecular weight less than about 750 000 daltons to a stem cell donor for increasing the concentration of stem cells in the blood of the donor.

U.S. Pat. No. 7,446,100 describes administration of hyaluronic acid having molecular weight less than about 750 000 daltons to a patient for mobilizing different blood cell types, such as lymphocytes, T- and/or B-cells into the blood of the patient.

Patent application US 2004/0204384 describes a method of regulating the differentiation of hematopoietic cells with a polymer of disaccharides comprised of an N-acetyl-D-glucosamine structure bonded by an O-glycoside β1-4 bond with a glucuronic acid structure.

BRIEF DESCRIPTION OF THE INVENTION

The present invention relates to a combination and/or combined use of at least one sulphated hyaluronan oligomer and/or polymer (a sulphated HAmer) and at least one factor capable of releasing stem cells. Particularly, the present invention relates to a combination and/or combined use of a sulphated hyaluronic acid oligomer and/or polymer (HAmer) and at least one factor capable of releasing stem cells. The present invention also relates to a use of at least one sulphated HAmer and at least one factor capable of releasing stem cells, or a combination thereof, to alter the relative amounts of blood cells and/or the types of blood cells in a subject.

The present invention also relates to a use of at least one sulphated HAmer and at least one factor capable of releasing stem cells, or a combination thereof for repairing the blood count of a subject. Thus, the present invention relates to at least one sulphated HAmer and at least one factor capable of releasing stem cells, or a combination thereof for use in repairing the blood count of a subject The present invention further relates to a use of at least one sulphated HAmer and at least one factor capable of releasing stem cells, or a combination thereof, to mobilize stem cells to the bloodstream of the subject. Thus, the present invention relates to at least one sulphated HAmer and at least one factor capable of releasing stem cells, or a combination thereof, for use in mobilizing stem cells to the bloodstream of the subject.

The present invention relates to a method for altering the relative amounts of blood cells and/or the types of blood cells of a subject by administering at least one sulphated HAmer and at least one factor capable of releasing stem cells, or a combination thereof to said subject.

The present invention relates to a method of mobilizing stem cells to the bloodstream of a subject by administering at least one hyaluronan oligomer and/or polymer or at least one factor capable of releasing stem cells or the combination thereof to said subject.

The present invention also relates to a method of repairing and/or improving the blood count of a subject by administering at least one sulphated HAmer and at least one factor capable of releasing stem cells or a combination thereof to said subject.

The present invention additionally relates to a use of at least one non-sulphated and/or a sulphated HAmer to repair blood count and/or alter the relative amounts of blood cells and/or the types of blood cells in a subject. Thus, the present invention relates to at least one non-sulphated and/or a sulphated HAmer for use in repairing blood count and/or in altering the relative amounts of blood cells and/or the types of blood cells in a subject.

Further, the present invention relates to a method of repairing the blood count in a subject by administering at least one non-sulphated and/or a sulphated HAmer to said subject. The present invention also relates to a method of altering the relative amounts of blood cells and/or the types of blood in a subject by administering at least one non-sulphated and/or a sulphated HAmer to said subject.

The present invention relates to sulphated and/or non-sulphated HAmers having the general formula (I):

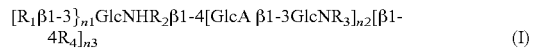

$$[R_1\beta 1\text{-}3]_{n1}\text{GlcNHR}_2\beta 1\text{-}4[\text{GlcA }\beta 1\text{-}3\text{GlcNR}_3]_{n2}[\beta 1\text{-}4R_4]_{n3} \quad (I)$$

wherein;

$R_1$ is an uronic acid non-reducing end group, which is GlcA or its beta-elimination product containing a double bond between 4- and 5-position of the uronic acid ring (delta-hexuroronic acid);

$R_2$ and $R_3$ are independently either H or acetyl or 3-10 C-alkyl or alkanoyl derivative of the amine or sulphate amide, the $R_3$ optionally varies at each position of the chain;

$R_4$ is a reducing end group, which is GlcA or its reducing end derivative including reducing (aldehyde form) and non-reducing (derivative of aldehyde) structures;

n1 and n3 are integers being either 0 or 1, n2 is an integer varying from 2-50, preferably 4-25, when n3 is 0 the reducing end GlcN is optionally derivatized as described for $R_4$;

the GlcN residue is optionally derivatized by sulphate residue at position 2 and/or 4 and/or 6, and HexA residue(s) is optionally derivatized by sulphate residue at position 2 and/or 3.

The objects of the invention are achieved by the methods, uses and compounds set forth in the independent claims. Preferred embodiments of the invention are described in the dependent claims.

Other objects, details and advantages of the present invention will become apparent from the following drawings, detailed description and examples.

A. Mice were treated with vehicle, 25 µg pegfilgrastim (Neulasta™) s.c., 500 µg LMW HA i.v or 500 µg LMW 6-O-S HA i.v. Samples were collected 4 hours after the injections.

B. Mice were treated as in A, but samples were collected either 1, 2 or 3 days after the injections. All time-points had time- and age-matched vehicle and Neulasta™ groups.

C. Mice were treated as in A, but samples were collected 5 days after the injections.

Figure 3:
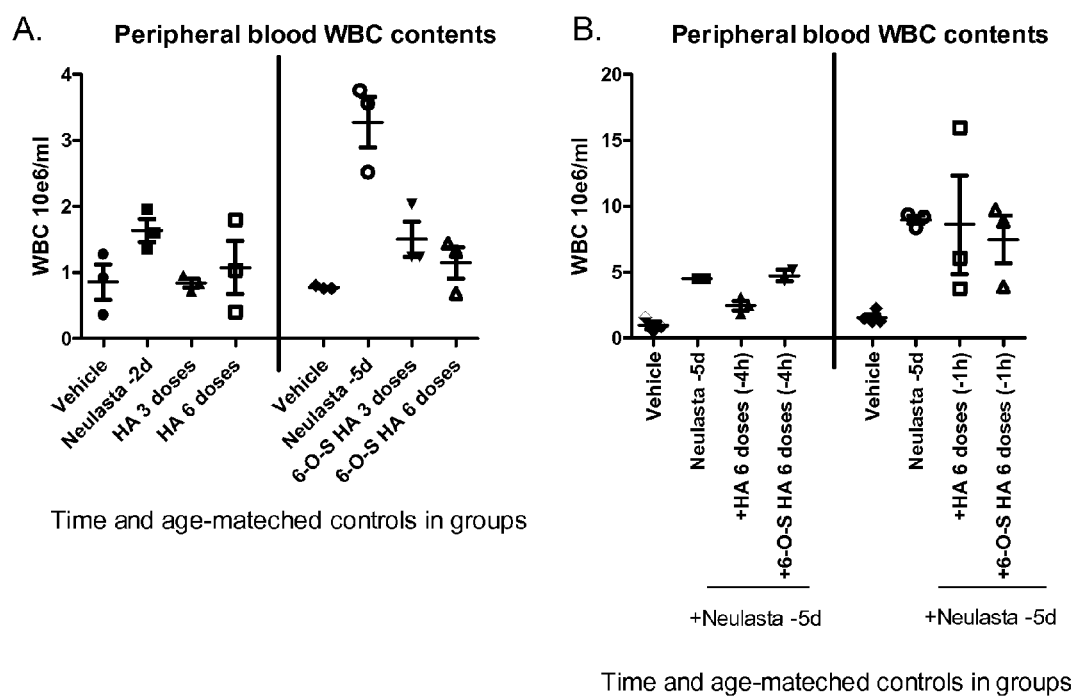

FIG. 3 shows the leukocyte (WBC) contents in mouse blood determined by automated blood cell counter Sysmex XT-2000i. Results are presented as scatter dot plots with means±SEM, with each point representing the value from a single mouse.

A. Mice were treated with vehicle, 25 µg pegfilgrastim (Neulasta™) s.c. single injection, 500 µg LMW HA i.v administered repeatedly daily for 2 (3 doses) or 5 days (6 doses) or 500 µg LMW 6-O-S HA i.v administered repeatedly daily for 3 (3 doses) or 6 days (6 doses). Samples were collected either 3 days or 5 days after the beginning of the injections and after 4 hours after the last LMW HA injection.

B. Mice were treated with vehicle and pegfilgrastim (Neulasta™) as in A and combination therapy groups received pegfilgrastim (Neulasta™) s.c. at day 0 (−5 days from sampling) and i.v. injections of 500 µg LMW HA or LMW 6-O-S HA administered repeatedly once daily (6 doses). Samples were collected 4 hours after the last LMW HA injection on study day 5.

All time-points have time- and age-matched vehicle and Neulasta™ control groups.

Figure 4:
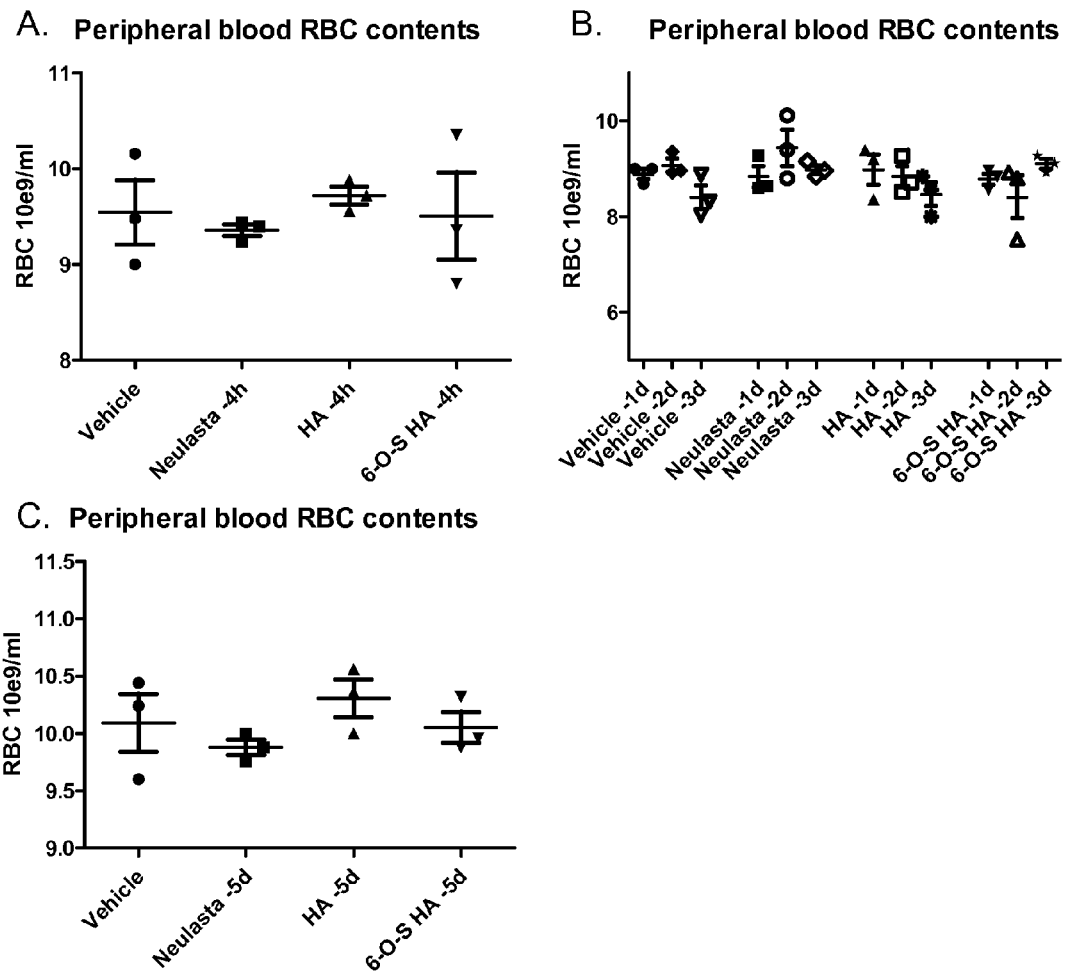

FIG. 4 shows the erythrocyte (RBC) contents in mouse blood determined by automated blood cell counter Sysmex XT-2000i. Results are presented as scatter dot plots with means±SEM, with each point representing the value from a single mouse.

A. Mice were treated with vehicle, 25 µg pegfilgrastim (Neulasta™) s.c., 500 µg LMW HA i.v or 500 µg LMW 6-O-S HA i.v. Samples were collected 4 hours after the injections.

B. Mice were treated as in A, but samples were collected either 1, 2 or 3 days after the injections. All time-points had time- and age-matched vehicle and Neulasta™ groups.

C. Mice were treated as in A, but samples were collected 5 days after the injections.

Figure 5:
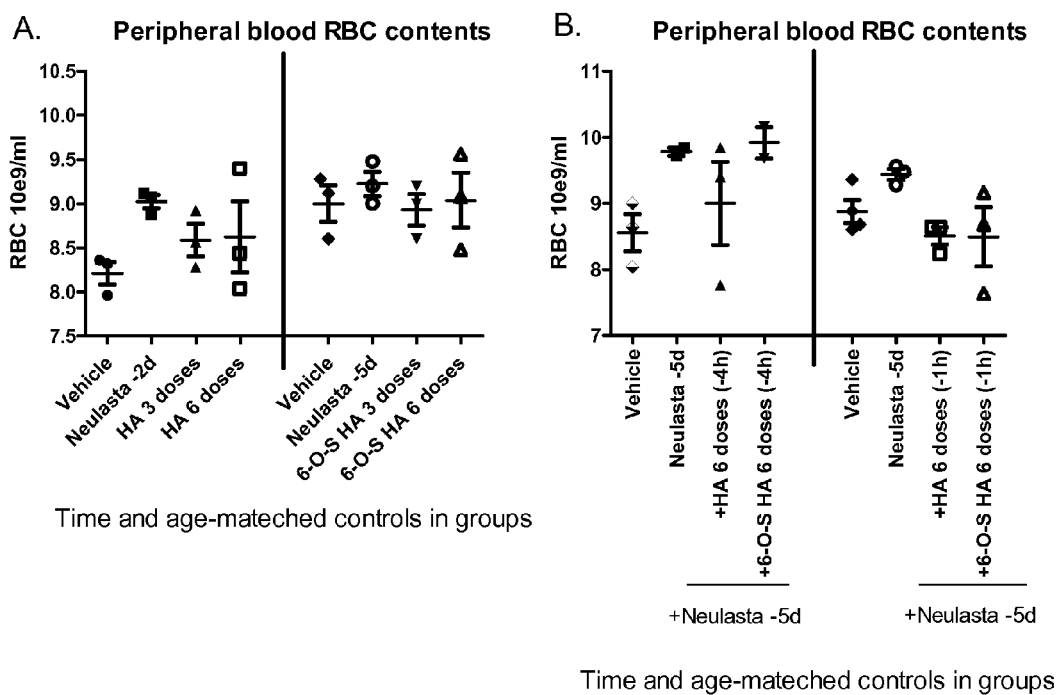

FIG. 5 shows the erythrocyte (RBC) contents in mouse blood determined by automated blood cell counter Sysmex XT-2000i. Results are presented as scatter dot plots with means±SEM, with each point representing the value from a single mouse.

A. Mice were treated with vehicle, 25 µg pegfilgrastim (Neulasta™) s.c. single injection, 500 µg LMW HA i.v administered repeatedly daily for 2 (3 doses) or 5 days (6 doses) or 500 µg LMW 6-O-S HA i.v administered repeatedly daily for 3 (3 doses) or 6 days (6 doses). Samples were collected either 3 days or 5 days after the beginning of the injections and after 4 hours after the last LMW HA injection.

B. Mice were treated with vehicle and pegfilgrastim (Neulasta™) as in A and combination therapy groups received pegfilgrastim (Neulasta™) s.c. at day 0 (−5 days from sampling) and i.v. injections of 500 µg LMW HA or LMW 6-O-S HA administered repeatedly once daily (6 doses). Samples were collected 4 hours after the last LMW HA injection on study day 5.

All time-points have time- and age-matched vehicle and Neulasta™ control groups.

Figure 6:
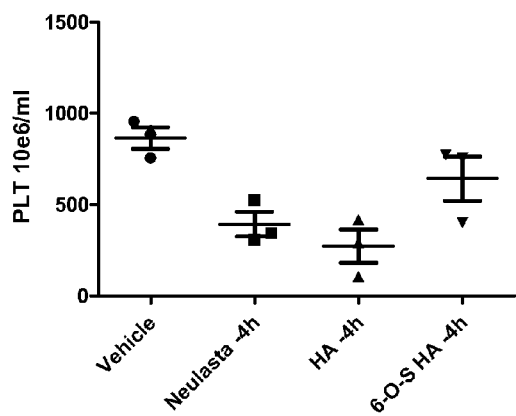
Figure 6:
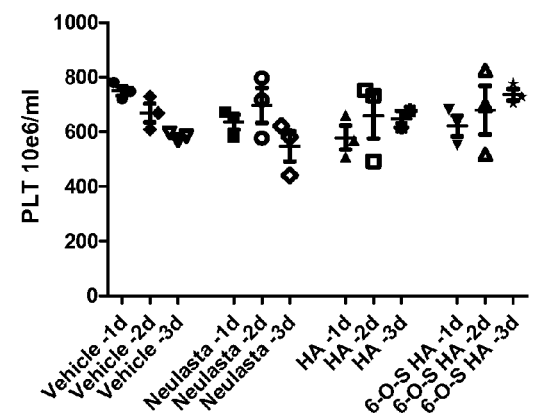
Figure 6:
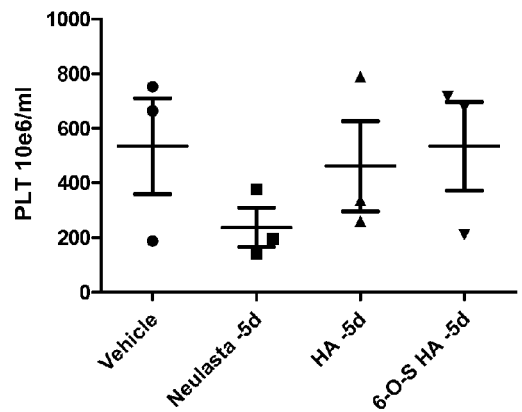

FIG. 6 shows the platelet (PLT) contents in mouse blood determined by automated blood cell counter Sysmex XT-2000i. Results are presented as scatter dot plots with means±SEM, with each point representing the value from a single mouse.

A. Mice were treated with vehicle, 25 µg pegfilgrastim (Neulasta™) s.c., 500 µg LMW HA i.v or 500 µg LMW 6-O-S HA i.v. Samples were collected 4 hours after the injections.

B. Mice were treated as in A, but samples were collected either 1, 2 or 3 days after the injections. All time-points had time- and age-matched vehicle and Neulasta™ groups.

C. Mice were treated as in A, but samples were collected 5 days after the injections.

Figure 7:
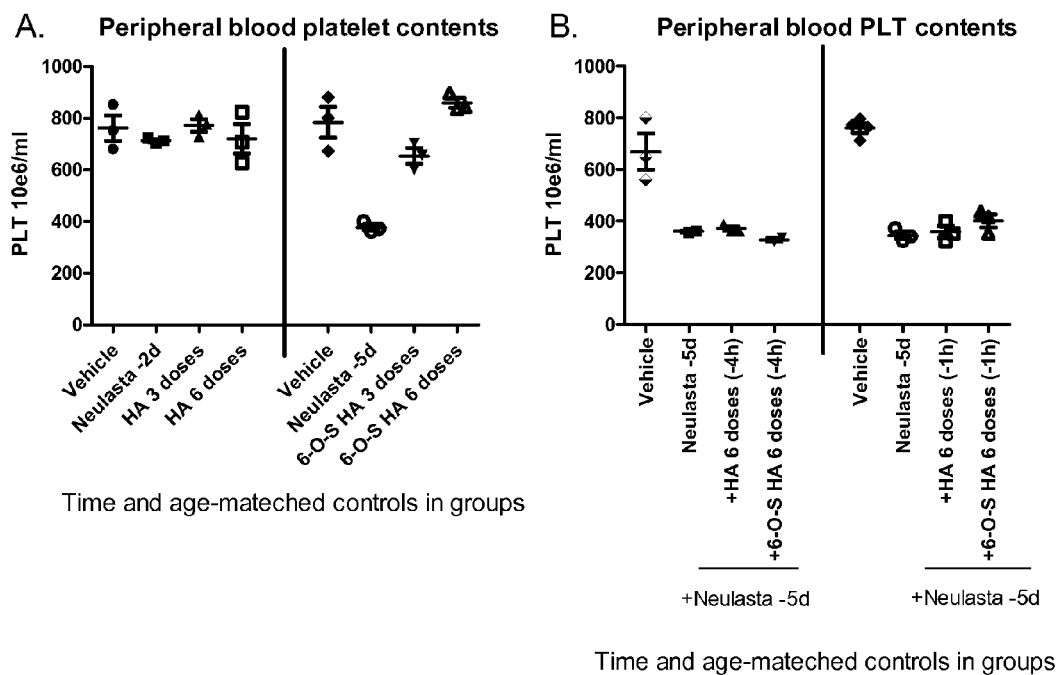

FIG. 7 shows the platelet (PLT) contents in mouse blood determined by automated blood cell counter Sysmex XT-2000i. Results are presented as scatter dot plots with means±SEM, with each point representing the value from a single mouse.

A. Mice were treated with vehicle, 25 µg pegfilgrastim (Neulasta™) s.c. single injection, 500 µg LMW HA i.v administered repeatedly daily for 2 (3 doses) or 5 days (6 doses) or 500 µg LMW 6-O-S HA i.v administered repeatedly daily for 3 (3 doses) or 6 days (6 doses). Samples were collected either 3 days or 5 days after the beginning of the injections and after 4 hours after the last LMW HA injection.

B. Mice were treated with vehicle and pegfilgrastim (Neulasta™) as in A and combination therapy groups received pegfilgrastim (Neulasta™) s.c. at day 0 (−5 days from sampling) and i.v. injections of 500 µg LMW HA or LMW 6-O-S HA administered repeatedly once daily (6 doses). Samples were collected 4 hours after the last LMW HA injection on study day 5.

All time-points have time- and age-matched vehicle and Neulasta™ control groups.

Figure 8:
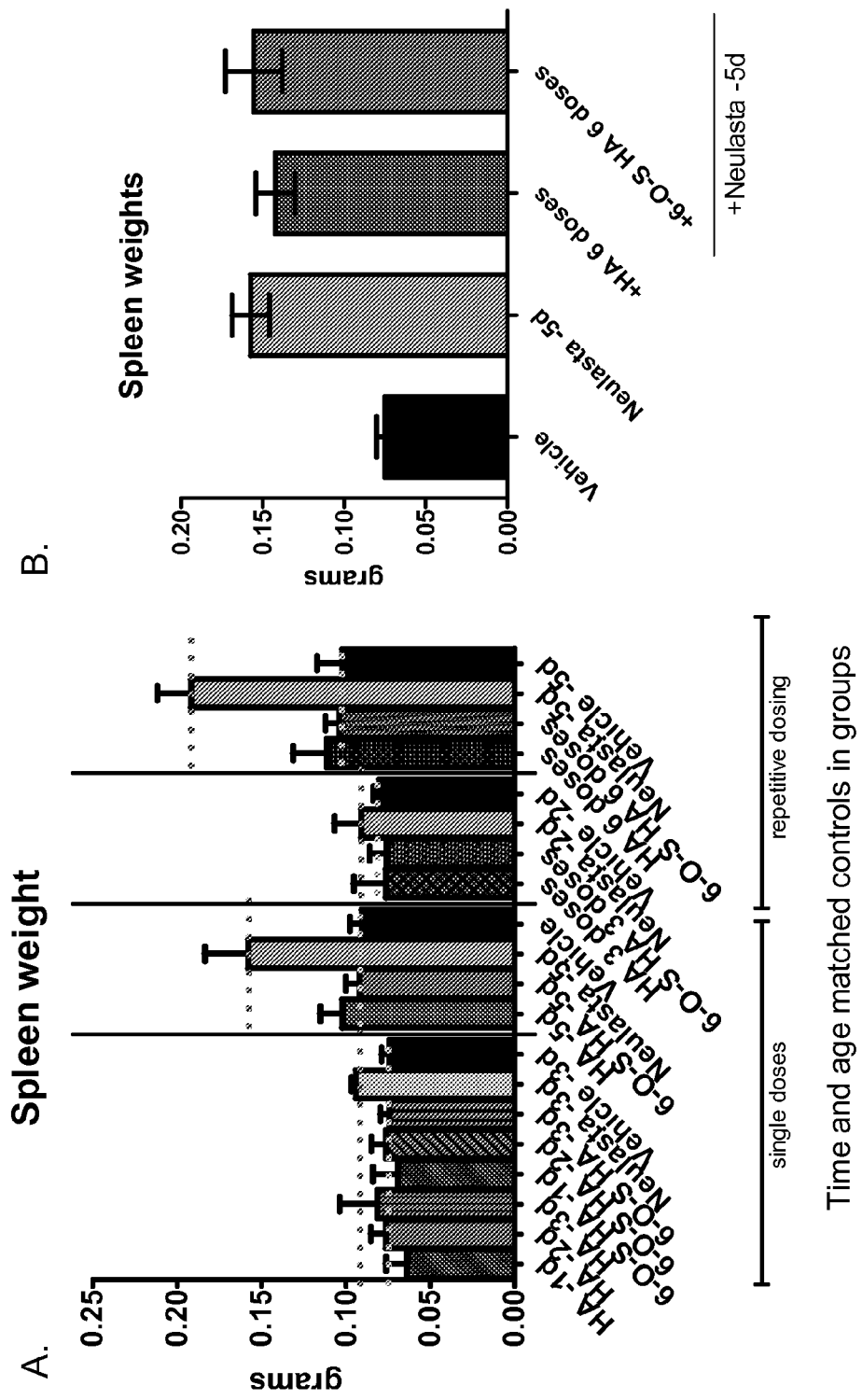

FIG. 8 shows the spleen weights in C57B1/6J mice after mobilization studies. The results presented are means±SD. All time-points have time- and age-matched vehicle and pegfilgrastim (Neulasta™) control animals.

A. LMW HA and LMW 6-O-S HA were administered in 500 µg doses/mouse i.v. either as single doses or repeatedly once/day for 2 (3 doses) or 5 (6 doses) days. Neulasta™ was injected as single 25 µg doses s.c. on study day 0. Vehicle animals were injected with similar injection schemes as the test substances. The animals were sacrificed 4 hours after the last injection on the last experimental day.

B. Mice were treated with vehicle and pegfilgrastim (Neulasta™) as in A and combination therapy groups received pegfilgrastim (Neulasta™) s.c. at day 0 (−5 days from sampling) and i.v. injections of 500 µg LMW HA or LMW 6-O-S HA administered repeatedly once daily (6 doses). Samples were collected 4 hours after the last LMW HA injection on study day 5.

Figure 9:
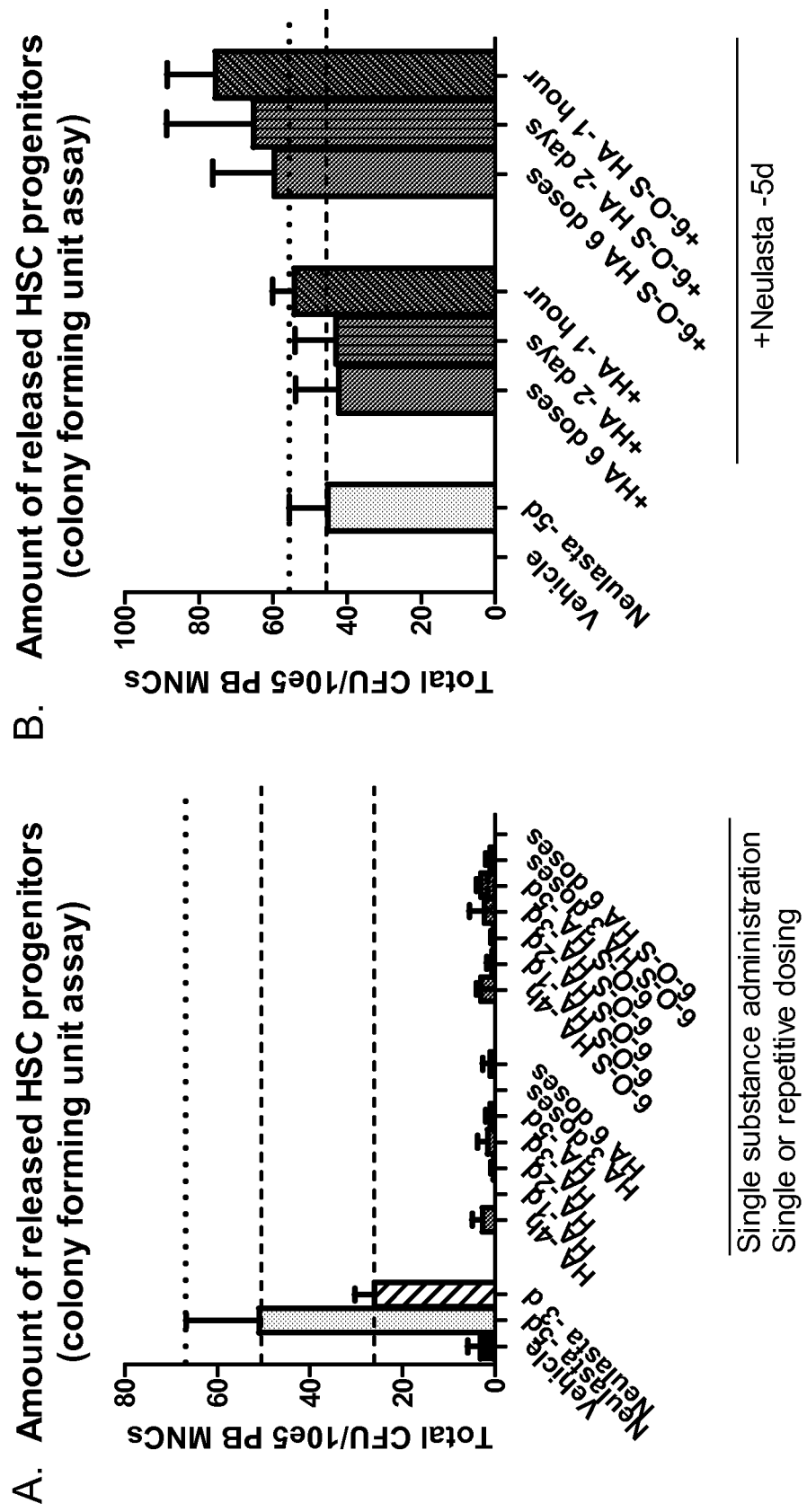

FIG. 9 shows the number of HPCs as determined by colony forming unit (CFU) assay. Peripheral blood mononuclear cells from C57B1/6J mice were isolated by Ficoll density centrifugation. $1 \times 10^5$ mononuclear cells were plated in duplicate and the total CFU amounts were counted 8-10 days after plating. The results presented are means±SD. All time-points have time- and age-matched vehicle and pegfilgrastim (Neulasta™) control animals.

A. LMW HA and LMW 6-O-S HA were administered in 500 µg doses/mouse i.v. either as single doses or repeatedly once/day for 2 (3 doses) or 5 (6 doses) days. Neulasta™ was injected as single 25 µg doses s.c. on study day 0. Vehicle animals were injected with similar injection schemes as the test substances. The animals were sacrificed 4 hours after the last injection on the last experimental day.

B. Mice were treated with vehicle and pegfilgrastim (Neulasta™) as in A and combination therapy groups received pegfilgrastim (Neulasta™) s.c. at day 0 (−5 days from sampling) and i.v. injections of 500 µg LMW HA or LMW 6-O-S HA administered repeatedly once daily (6 doses) or as single doses 2 days before or 1 hour before sampling. n=3 mice/group.

Figure 10:
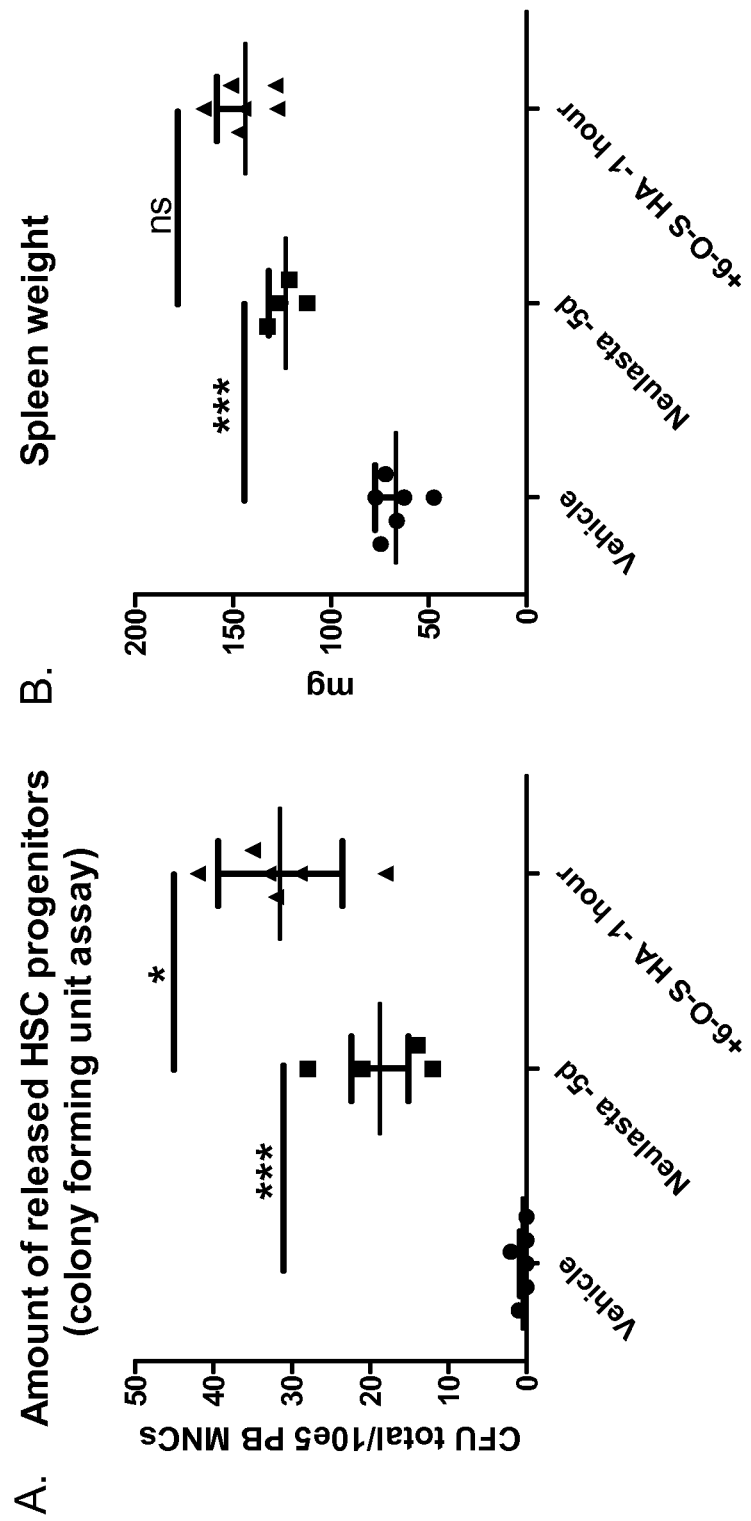

FIG. 10 shows the number of HPCs as determined by colony forming unit (CFU) assay. Peripheral blood mononuclear cells from C57B1/6J mice were isolated by Ficoll density centrifugation. $1 \times 10^5$ mononuclear cells were plated in duplicate and the total CFU amounts were counted 8-10 days after plating. Results are presented as scatter dot plots and means±SD, with each point representing the value from a single mouse (n=4-6). All time-points have time- and age-matched vehicle and pegfilgrastim (Neulasta™) control animals.

A. Neulasta was injected as single 25 µg doses s.c. on study day 0. The combination therapy group (+6-O-S HA) received pegfilgrastim (Neulasta™) s.c. at day 0 (−5 days from sampling) and a single i.v. injection of 500 µg LMW 6-O-S HA administered 1 hour before sampling.

B. Spleen weights in the same animals as were studied in A. Results are presented as scatter dot plots and means±SD, with each point representing the value from a single mouse ±SD (n=4-6).

Figure 11:
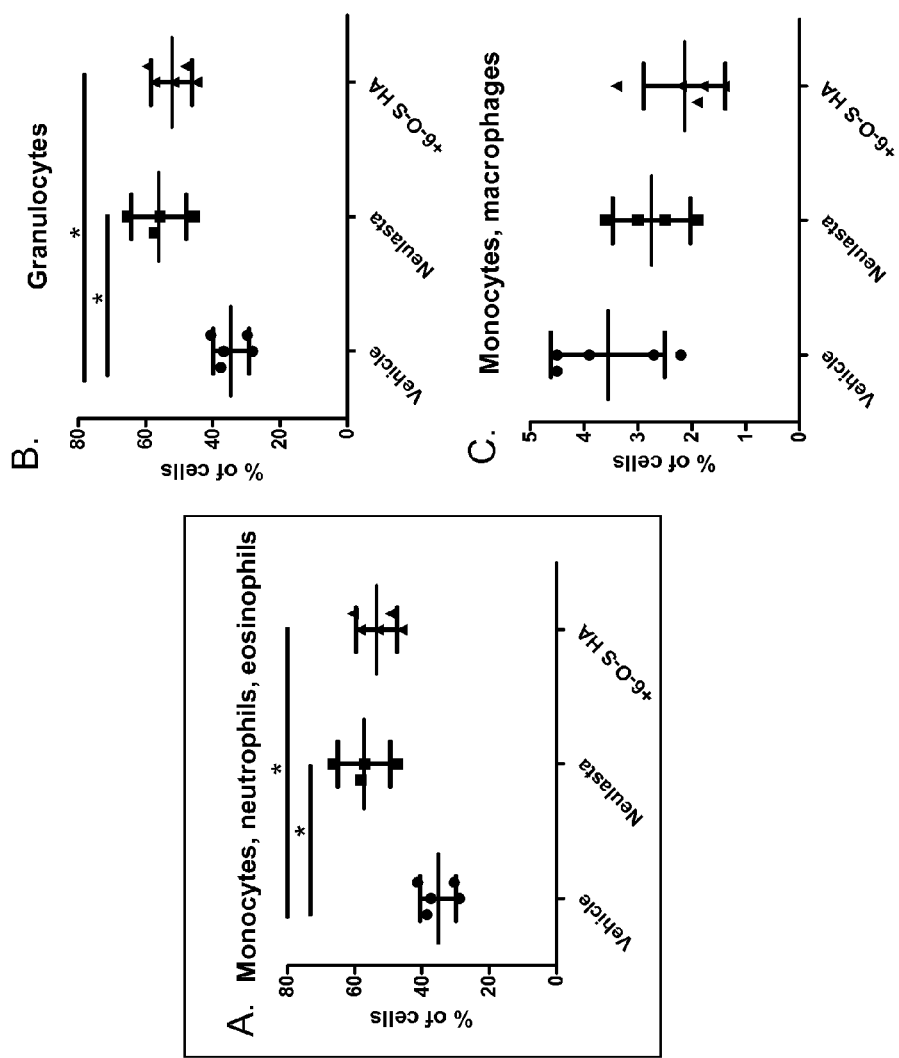

FIG. 11 shows the immunophenotypic profiling of monocytes, neutrophils and eosinophils (MNEs) in peripheral blood after mobilization studies as studied by flow cytometry. The cells gated in A. were further analyzed in B. and C. Neulasta™ was injected as single 25 µg doses s.c. on study day 0. The combination therapy group (+6-O-S HA) received pegfilgrastim (Neulasta™) s.c. at day 0 (−5 days from sampling) and a single i.v. injection of 500 µg LMW 6-O-S HA administered 1 hour before sampling. Results are presented as scatter dot plots with means±SEM, with each point representing the value from a single mouse (n=4-5).

Figure 12:
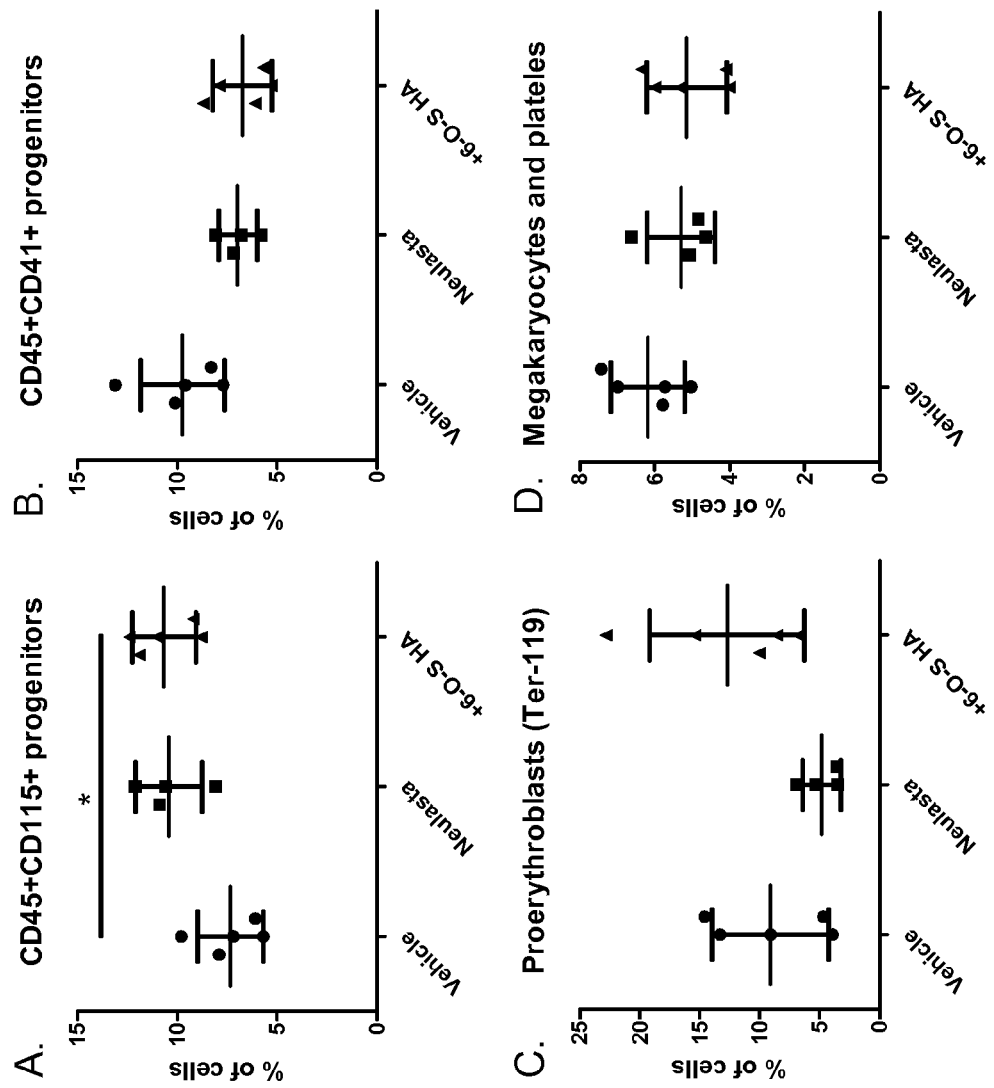

FIG. 12 shows the immunophenotypic profiling of peripheral blood after mobilization studies as studied by flow cytometry. Lymphocytic cell population was excluded from the analysis. Neulasta™ was injected as single 25 µg doses s.c. on study day 0. The combination therapy group (+6-O-S HA) received pegfilgrastim (Neulasta™) s.c. at day 0 (−5 days from sampling) and a single i.v. injection of 500 µg LMW 6-O-S HA administered 1 hour before sampling. Results are presented as scatter dot plots with means±SEM, with each point representing the value from a single mouse (n=4-5).

Figure 13:
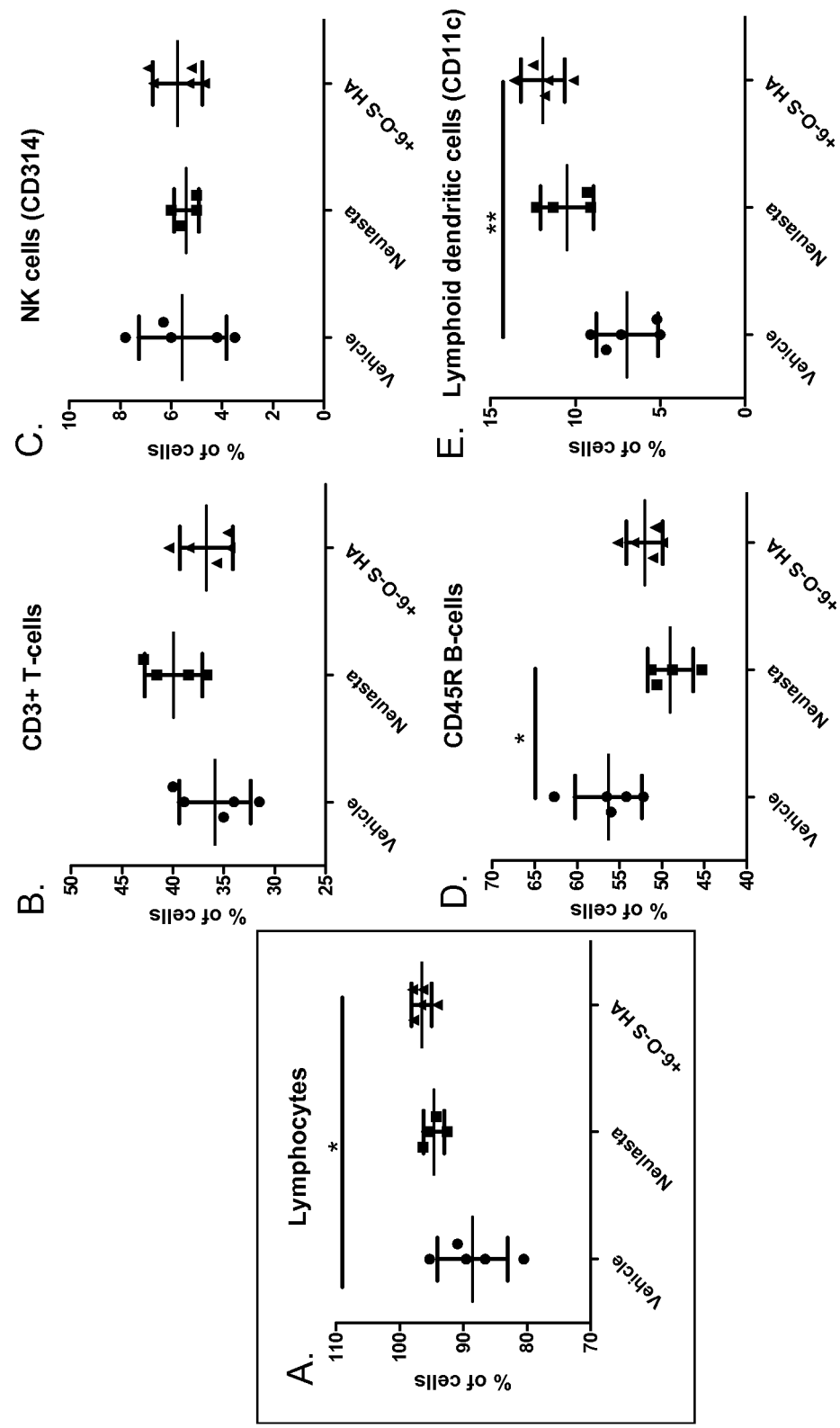

FIG. 13 shows the immunophenotypic profiling of lymphocytes in peripheral blood after mobilization studies as studied by flow cytometry. The cells gated in A. were further analyzed in B-E. Neulasta™ was injected as single 25 µg doses s.c. on study day 0. The combination therapy group (+6-O-S HA) received pegfilgrastim (Neulasta™) s.c. at day 0 (−5 days from sampling) and a single i.v. injection of 500 µg LMW 6-O-S HA administered 1 hour before sampling. Results are presented as scatter dot plots with means±SEM, with each point representing the value from a single mouse (n=4-5).

Figure 14:
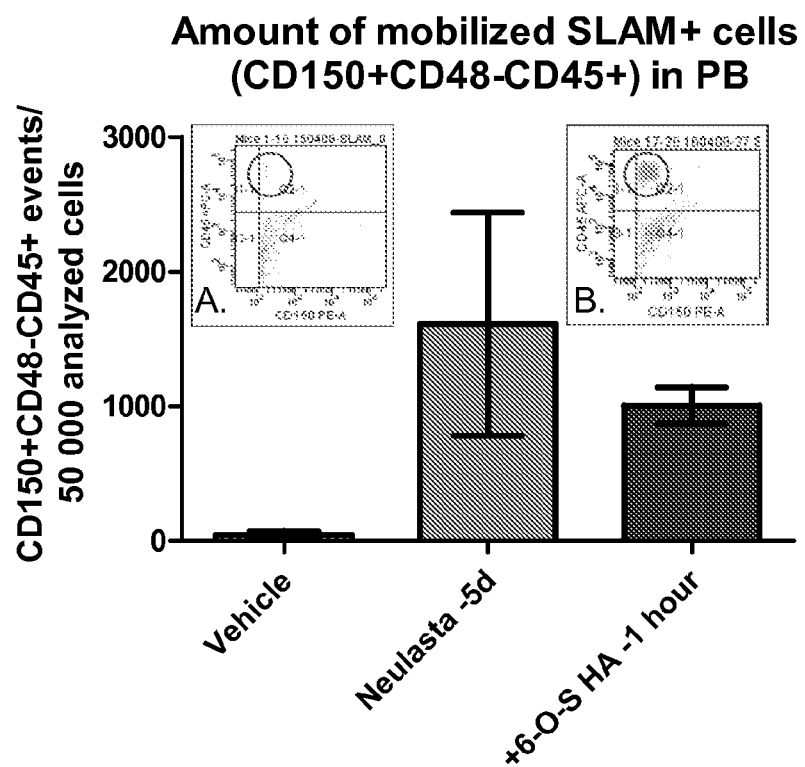

FIG. 14 shows the amounts of SLAM+ cells (CD150+ CD48−CD45+) in peripheral blood. The results are presented as means±SD of recorded positive events/50 000 analyzed cells. Neulasta™ was injected as single 25 µg doses s.c. on study day 0. The combination therapy group (+6-O-S HA) received pegfilgrastim (Neulasta™) s.c. at day 0 (−5 days from sampling) and a single i.v. injection of 500 µg LMW 6-O-S HA administered 1 hour before sampling. Inset A. represents the analyzed cell population in the vehicle group and inset B. represents the analyzed cell population in the Neulasta™-alone and Neulasta™+6-O-S HA-groups.

Figure 15:
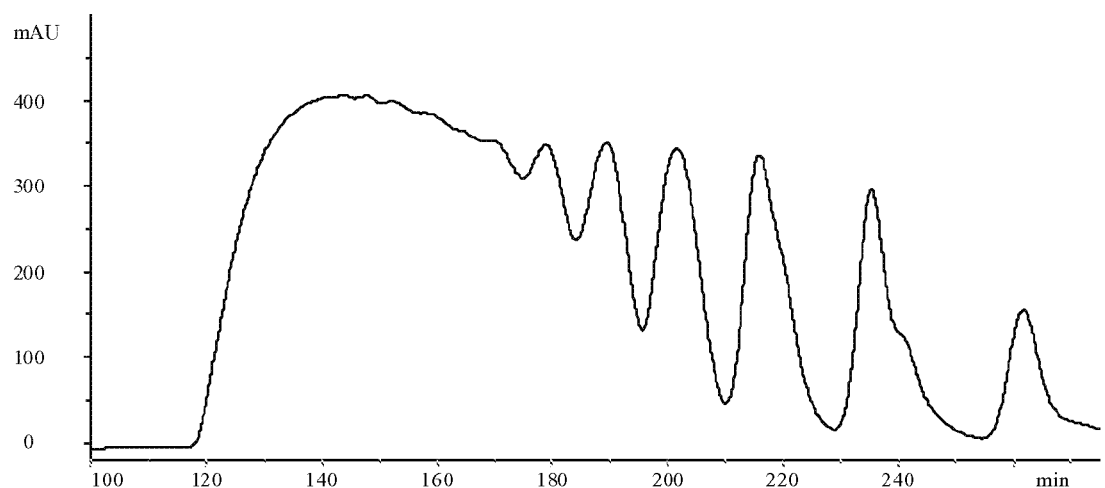

FIG. 15 shows the fractionation of acid hydrolyzed hyaluronic acid by size exclusion HPLC on preparative Superdex column.

Figure 16:
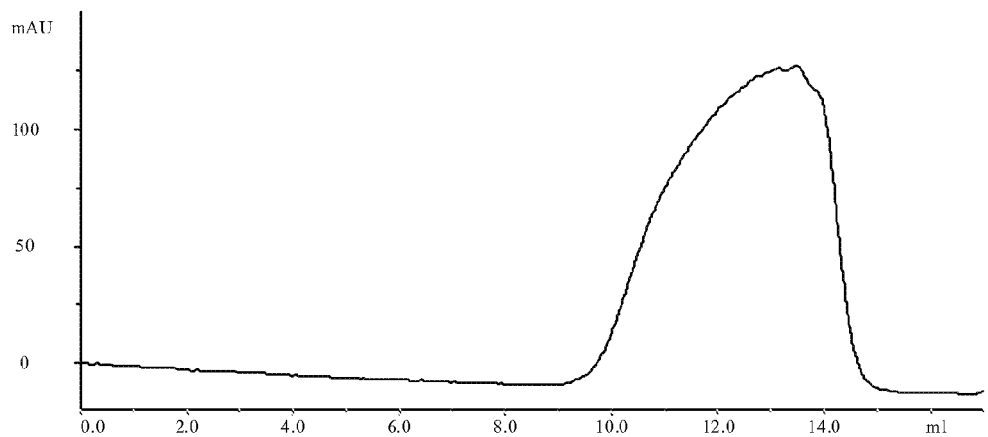
Figure 16:
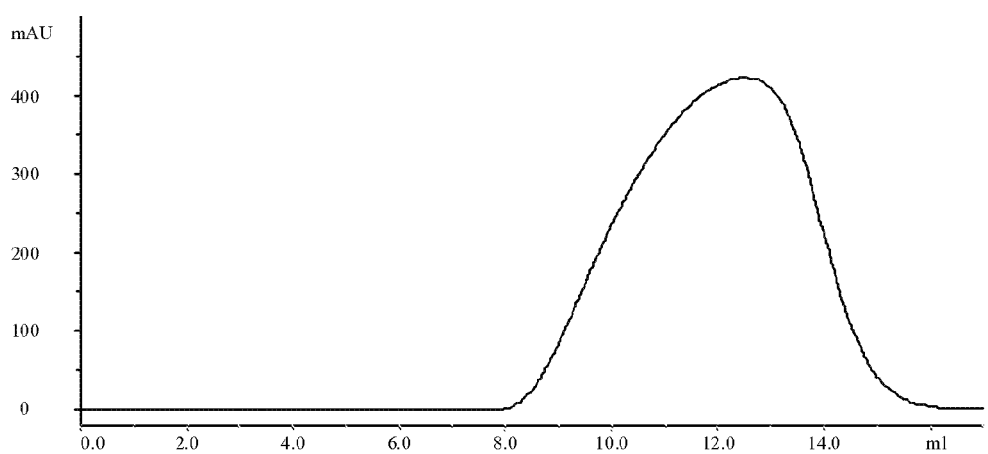
Figure 16:
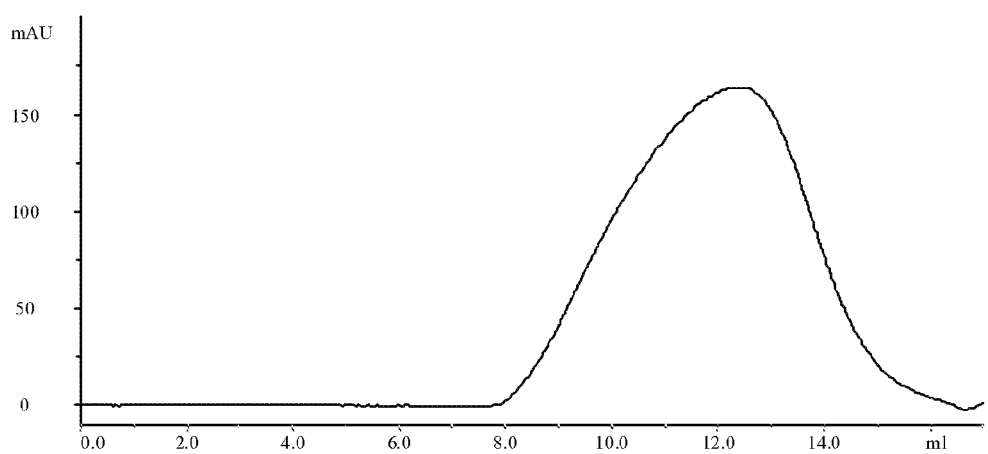

FIG. 16 shows the analysis of hyaluronic acid and sulfated hyaluronic acid preparates by size exclusion HPLC on Superdex 75 column.

A. Acid-hydrolyzed and fractionated 10 mer to 46 mer hyaluronic acid.
B. 4.8 kDa hyaluronic acid.
C. 50% 6-O-sulfated 4.8 kDa hyaluronic acid.

DETAILED DESCRIPTION OF THE INVENTION

Stem cells are characterized by their ability to renew themselves and to differentiate into a diverse range of specialized cell types. Hematopoietic stem cells (HSC) are pluripotent (or multipotent) cells having ability to form all the blood cell types including myeloid and lymphoid lineages. HCSs are currently used for treating certain hematological and non-hematological diseases. HSCs can be derived for example from bone marrow and cord blood. Mesenchymal stem cells (MSC) have the potential to differentiate into various cellular lineages and can be expanded in culture conditions without losing their multipotency. Therefore, they present a valuable source for applications in cell therapy and tissue engineering. MSCs can be derived for example from bone marrow. Endothelial stem cells are multipotent stem cells and one of the three types of stem cells to be found in bone marrow. Human embryonic stem cells (hESCs) are derived from the inner cell mass of 3-5 day-old blastocysts. hESCs are considered to be the building blocks for all types of cells in humans and thus have huge potential in applications of cell therapy and regenerative medicine. Induced pluripotent stem (iPS) cells are a type of pluripotent stem cell artificially derived from a non-pluripotent cell, typically an adult somatic cell by inducing a "forced" expression of certain genes.

In the present invention, the term "stem cell" refers mainly to stem cells found in blood, and/or derived or derivable from blood, and/or releasable to blood by reagents and methods described in the invention, such as hematopoietic, mesenchymal, and/or endothelial stem cells.

Factors and/or agents capable of releasing stem cells from the site of origin, typically bone marrow, are used to mobilize stem cells into circulation and increase their number in peripheral blood, thus allowing a more efficient collection of larger number of stem cells from the circulation. Cytokines, such as, granulocyte-colony-stimulating factor (G-CSF) and granulocyte-macrophage colony-stimulating factor (GM-CSF), and CXCR4-receptor inhibitors, such as, plerixafor (Mozobil™) are examples of factors and/or agents that are capable of mobilizing stem cells into circulating blood of a subject.

Granulocyte-colony-stimulating factor (G-CSF) is a glycoprotein regulating the production and release of stem cells from the bone marrow. It is currently the most widely used cytokine for mobilizing stem cells into peripheral blood. The effect of G-CSF can be seen after 4 to 5 days after its administration. G-CSF is known to stimulate the production of white blood cells (WBC). G-CSF is used with certain cancer patients to accelerate recovery from neutropenia after chemotherapy, allowing higher-intensity treatment regimens. G-CSF is also used to increase the number of hematopoietic stem cells in the bloodstream of a subject (a donor) before collecting and using the cells in stem cell transplantation. G-CSF may also be given to a recipient of a hematopoietic stem cell transplant.

Pegfilgrastim (Neulasta™) is a covalent conjugate of recombinant human G-CSF (r-metHuG-CSF) with a single 20 kd polyethylene glycol (PEG) molecule. Pegfilgrastim is approved by European Medicines Agency (EMEA) for reduction in the duration of neutropenia and the incidence of febrile neutropenia in patients treated with cytotoxic chemotherapy for malignancy (with the exception of chronic myeloid leukaemia and myelodysplastic syndromes).

Granulocyte-macrophage colony-stimulating factor (GM-C SF) is a glycoprotein regulating the production and release of stem cells. It stimulates stem cells to produce granulocytes and monocytes.

In the present invention, the granulocyte-colony-stimulating factor (G-CSF) and the granulocyte-macrophage colony-stimulating factor (GM-CSF) include therapeutically suitable and/or pharmaceutically acceptable derivates, conjugates and analogs, such as, pegylated, glycopegylated and glycan conjucated variants.

In one embodiment of the invention, the factor capable of mobilizing stem cells is G-CSF or GM-C SF.

CXCR4 inhibitors, such as, plerixafor (Mozobil™) act by blocking CXCR4-receptors and aid in releasing stem cells into circulating blood. CXCR4 is a chemokine receptor that plays an important role in holding hematopoietic stem cells in the bone marrow.

In the present invention, the term "factor capable of mobilizing stem cells" or the term "factor mobilizing stem cells" refer to a molecule, such as a cytokine and/or to a compound (an antagonist or an inhibitor) able to induce the release of stem cells by blocking a receptor, that is capable to hold stem cells in their place of origin, for example, in the bone marrow.

In one embodiment of the invention, the factor mobilizing stem cells is a cytokine or a CXCR4-receptor inhibitor/antagonist including therapeutically suitable and/or pharmaceutically acceptable derivates, conjugates and analogs, such as, pegylated, glycopegylated and glycan conjucated variants thereof.

In one embodiment of the invention, the factor mobilizing stem cells into circulation is selected from the group of G-CSF, GM-CSF, CXCR4-receptor inhibitors/antagonists, their derivatives, analogs and conjugates and/or mixtures thereof.

Hyaluronan oligomers and/or polymers (HAmers) are unbranched polysaccharides that consist of repeating disaccharide units. Hyaluronic acid (HA) is composed of D-glucuronic acid (GlcA) and N-acetylglucosamine (GlcNAc) linked together via alternating β-1,4 and β-1,3 glycosidic bonds. Hyaluronic acid can be 25 000 disaccharide repeats in length. Polymers of hyaluronic acid can range in size from 5 000 to 20 000 000 Da in vivo. Hyaluronic acid is naturally non-sulphated.

The present invention is directed to novel low molecular weight fragments of hyaluronic acid (LMW HA) including polymers and/or oligomers or mixtures thereof having molecular weights less than about 25 000 Da, preferably less than 15 000 Da, more preferably less than 10 000. In one embodiment of the invention, the LMW HAmer is a HAmer or a mixture of HAmers having molecular weight on average about 5000 Da or less.

In one embodiment of the invention, the structure of the hyaluronic acid oligomer and/or polymer of the present invention is described in Formula (I):

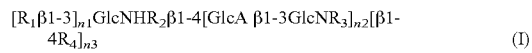

$$[R_1\beta 1\text{-}3]_{n1}\text{GlcNHR}_2\beta 1\text{-}4[\text{GlcA } \beta 1\text{-}3\text{GlcNR}_3]_{n2}[\beta 1\text{-}4R_4]_{n3} \qquad (I)$$

wherein;

$R_1$ is non-reducing group, which is GlcA or its beta-elimination product containing a double bond between 4- and 5-position of the uronic acid ring (delta-hexuroronic acid);

$R_2$ and $R_3$ are independently either H or acetyl or 3-10 C-alkyl or alkanoyl derivative of the amine or sulphate amide, the $R_3$ may also vary at each position of the chain;

$R_4$ is a reducing end group, which is GlcA or its reducing end derivative including preferably reducing (aldehyde containing) and non-reducing (aldehyde derivative) reducing end structures;

n1 and n3 are integers being either 0 or 1, n2 is an integer varying from 2-50, preferably 4-25, when n3 is 0 the reducing end GlcN may be derivatized as described for $R_4$;

the GlcN residue may be further derivatized by sulphate residue at position 2 and/or 4 and/or 6, more preferably to 6-position, and GlcA residue(s) may be optionally derivatized by sulphate residue at position 2 and/or 3.

Low molecular weight (LMW) HAmer refers to a HAmer and/or a mixture of HAmers comprising from 2 to 100, preferably from 2 to 50, and more preferably from 4 to 25 dimer-units.

Sulphated low molecular weight hyaluronic acid (LMW 6-O-S HA) refers to a hyaluronic acid oligomer and/or polymer or as mixture thereof comprising from 2 to 100, preferably from 2 to 50, and more preferably from 4 to 25 dimer-units that are sulphated i.e., carry a sulphate-group attached to the N-acetylglucosamine or optionally also glucosamine-unit of the dimer. The sulphation level of the HAmer of the present invention is from about 0.1 to about 1.5. In one embodiment of the present invention, the average sulphation level is between about 0.15 to about 1.0 sulphate residues per a dimer. The sulphate group is preferably esterified to 6 positions of GlcNR— residues. The preferred active 6-sulphated hyaluronic acid may further comprise partially de-N-acetylated structures, which may be N-sulphated or glucosamine (GlcN)-residues without amine sulphation. In one embodiment, the amount of GlcN and/or N-sulpahated GlcN residues is less than about 20% of the GlcNR residues, preferably the amount of GlcN with amine function, is between 0.1-20%, more preferably between 0.2-20% or most preferably between 1 and 15%. In a specific embodiment at least 5% of the GlcN-residues are N-sulphated. The amine function or its sulphated derivative are favoured for chemical production and/or modulation of bioactivity.

The HAmers are preferably specifically 6-sulphated so that at least 50%, more preferably at least 70%, even more preferably at least 80%, even more preferably at least 90%, and most preferably at least 95% of sulphate is linked to the 6-position of GlcN(Ac). Preferred 6-sulphation levels are from about 0.1 to about 1.0, more preferably from about 0.15 to about 1.0 sulphate residues per a dimer. In a specific embodiment the sulphation level is medium level preferably from about 0.20 to about 0.9 sulphate residues, more preferably from about 0.25 to about 0.80 sulphate residues per a dimer of the glycan backbone. The number of glycan backbone dimers is defined by variable n2 of Formula I.

In another preferred embodiment the invention is directed to essentially non-sulphated HAmers of Formula I, preferably comprising less than 0.2 sulphate residues per dimer defined by n2 of Formula I, more preferably less than 0.1 sulphate residues, and in a specific embodiment less than 0.03 sulphate residues. In specific embodiment the specific sulphated forms, especially 6-sulphate forms are favoured for chemical production and/or modulation of bioactivity.

In a preferred embodiment the HAmer of the present invention comprise non-reducing end $R_1$ (GlcA or derivative, n1 of Formula I is 1) and further preferably reducing end $GlcNR_3$ (n3 of Formula I is 0). In a preferred embodiment at least 60%, more preferably at least 70%, even more preferably at least 80%, even more preferably at least 90%, and most preferably at least 95% of the non-reducing end residues are GlcA and/or at least 60%, more preferably at least 70%, even more preferably at least 80%, even more preferably at least 90%, and most preferably at least 95% of the reducing end residues are GlcN. Preferably the levels of the non-reducing end GlcA and reducing end GlcN are essentially similar (at least about 60, 70, 80, 90, or 95%). The reducing and non-reducing end structures are favoured for effective chemical synthesis and benefits in bioactivity, uniformity and standardization of the therapeutic substances.

In one aspect, the present invention is based on a surprising finding that a sulphated HAmer can be used to enhance and/or improve the effect of a factor capable of mobilizing stem cells in releasing the stem cells from their place of origin, typically from the bone marrow, into the blood circulation. In one embodiment, the object of the present invention to provide a combination or a combined use of a sulphated HAmer and a factor capable of mobilizing stem cells. A sulphated HAmer suits to be used in combination with a factor mobilizing stem cells to mobilize and/or release stem cells to the bloodstream for collection and subsequent transplantation in patients suffering from cancers, such as leukemias, lymphomas and myelomas. The use of a sulphated HAmer in combination with at least one factor capable of mobilizing stem cells provides an enhancement for the treatment of cancers that require a stem cell transplant. The therapeutic indications for the combination and/or combined use of a sulphated HAmer and at least one factor capable of mobilizing stem cells include mobilization of stem cells for autologous and/or allogenic transplants and tumor sensitization in oncological and hematological maladies. Further, according the present invention, the HAmers are suited for treating conditions requiring immunomodulation, such as, therapeutic immunomodulation in context of cancer treatments, or for preventing side effects of blood cell donation and/or blood cell count or content modulation e.g. by growth factors such as G-CSF. Side effects, such as, anemia or reduced immunodefence/immunosuppression or autoimmune reactions are typical especially in context of growth factor treatments. As a consequence of the combined use of a sulphated HAmer and at least one factor capable of mobilizing stem cells, the amount or content of the factor mobilizing stem cells can be reduced and/or lowered, the number of stem cells in peripheral blood is increased, and/or the number of apheresis sessions or the duration of the sessions for harvesting the minimum number of cells (approximately 2 million stem cells/kg of body weight) can be reduced. Accordingly, the combination or combined use of at least one sulphated HAmer and at least one factor capable of mobilizing stem cells is more efficient than a factor mobilizing stem cells alone in mobilizing and collecting the optimal number of stem cells for transplantations. The advancements and advantages the combination or combined use of the present invention provides for the treatment of certain malignant diseases and cancers requiring stem cell transplantation include more rapid collections of stem cells, larger numbers of stem cells and faster recovery times.

In one embodiment, the present invention relates to an in vivo method for producing the mobilisation of stem cells into a bloodstream in subject, wherein said method comprises administering at least one sulphated hyaluronan oligomer and/or polymer (HAmer) to the subject and administering at least one factor capable of releasing stem cells to the subject. In one embodiment of the method of the invention, the factor capable of releasing stem cells is G-CSF or GM-CSF In another embodiment of the invention, the combination is used to alter or modulate the relative amounts of blood cells and/or the types of blood cells or the HAmer and the factor mobilizing stem cells are used in combination to alter or modulate the relative amounts of blood cells and/or the types of blood cells. In yet another embodiment, the combination is used for repairing or improving the blood count of a subject or the HAmer and the factor mobilizing stem cells are used in combination for repairing or improving the blood count of a subject. In still another embodiment of the invention, the combination is used to mobilize stem cells to the bloodstream of the subject, typically from the bone marrow or the HAmer and the factor mobilizing stem cells are used in combination to mobilize stem cells to the bloodstream of the subject, typically from the bone marrow. The combination or combined use of a sulphated HAmer and a factor capable of mobilizing stem cells, such as G-CSF in its pegylated form (Neulasta™) has shown an unexpected positive co-operative action. Pegylated C-GSF is known to have good activity in avoiding graft versus host disease, and the combination and/or combined use of the invention showed enhanced immunomodulatory effects. In a preferred embodiment, the sulphated HAmer is a low molecular weight sulphated HAmer. In another preferred embodiment, the factor capable of mobilizing stem cells is G-CSF and/or its therapeutically suitable and/or pharmaceutically acceptable derivates, conjugates and analogs, such as, pegylated G-CSF.

It is also an object of the present invention to provide a method for altering the relative amounts of blood cells and/or the types of blood cells of a subject by administering a sulphated HAmer and a factor capable of mobilizing stem cells or the combination thereof to said subject. In one embodiment, the present invention relates to a method of altering the relative amounts of blood cells and/or the types of blood cells. In another embodiment, the present invention relates to a method for repairing the blood count of a subject by administering a sulphated HAmer and a factor capable of mobilizing stem cells or the combination thereof to said subject. In a further embodiment, the present invention relates to a method of mobilizing stem cells to the bloodstream by administering a sulphated HAmer and a factor capable of mobilizing stem cells or a combination thereof to said subject. In one embodiment of the invention, the factor capable of releasing stem cells is G-CSF or GM-CSF. In another embodiment of the invention, the HAmer contains from 2 to 50, preferably from 4 to 25 dimer units.

In another aspect, the present invention is based on a surprising finding that a non-sulphated and/or a sulphated HAmer can be used for altering the relative amounts or numbers of different blood cells and/or the types of blood cells such as white blood cells, red blood cells and platelets. White blood cells or leucocytes can be divided into granulocytes (polymorphonuclear leukocytes) and agranulocytes (mononuclear leucocytes). Granulocytes can be further divided into neutrophils, basophils and easinophils. Agranulocytes include lymphocytes, monocytes and macrophages. The relative amounts or numbers of different blood cells and/or the types of blood cells differ in and/or are indicative to certain hematological and/or oncological diseases or emergencies. Thus, the HAmers are suited for treating conditions requiring immunomodulation, such as, therapeutic immunomodulation in context of cancer treatments, or for preventing side effects of blood cell donation and/or blood count or blood cell content modulation e.g. by growth factors such as G-CSF. There is no need to administer a factor mobilizing stem cells to a subject and accordingly, the adverse effects related to the use of factors capable of mobilizing stem cells, such as, anemia or reduced immunodefence/immunosuppression or autoimmune reactions that are typical especially in context of growth factor treatments, are avoided. It is thus, the object of the present invention to provide use of a non-sulphated and/or a sulphated HAmer for altering the relative amounts of blood cells and/or the types of blood cells in a subject. Another object of the present invention is to provide use of a non-sulphated and/or a sulphated HAmer for repairing the blood count of a subject.

When the sulphated HAmer is used in combination with a factor capable of mobilizing stem cells, it can be administered to a subject together with or separately from the administration of the factor mobilizing stem cells. When administered separately from the factor capable of mobilizing stem cells, the sulphated HAmer can be administered before, simultaneously or after the administration of the factor capable of mobilizing stem cells.

The HAmer and/or the factor mobilizing stem cells can be formulated to a pharmaceutical composition. The combination of at least one sulphated HAmer and at least one factor mobilizing stem cells can be formulated for example to a single dosage form preparation or a kit-type preparation depending on the mode of administration. In one embodiment of the invention, the pharmaceutical composition in a single dosage form preparation or a kit-type preparation comprises at least one HAmer and in another embodiment, at least one HAmer and at least one factor capable of mobilizing stem cells. In another embodiment of the invention, HAmer is formulated in a first formulation and the factor mobilizing stem cells is formulated in a second formulation, and the first and the second formulations are administered simultaneously or sequentially, in any order, to a subject. In one embodiment, HAmer is administered prior to administration of the factor mobilizing stem cells. In another embodiment, the factor mobilizing stem cells is administered prior to administration of the HAmer. In one embodiment of the invention, the factor capable of releasing stem cells is G-CSF or GM-CSF. In another embodiment of the invention, the HAmer contains from 2 to 50, preferably from 4 to 25 dimer units.

The pharmaceutical compositions may be used parenterally or enterally for example in liquid, semisolid or solid form such as in the form of a solution, an emulsion, a suspension, a tablet, a pellet or a capsule. In one embodiment the pharmaceutical composition is in a liquid form, such as an infusion solution, to be administered to blood circulation. The invention is especially directed to human acceptable infusion components including optionally physiological salts and/or nutrients. When the infusion comprises cytokines or factors capable of mobilizing stem cells, the infusion is formulated in order to keep the combination of the molecules soluble for effective infusion.

In addition to at least one HAmer of the invention and/or at least one factor capable of mobilizing stem cells, the pharmaceutical composition may comprise pharmaceutically acceptable carrier(s), adjuvant(s), excipient(s), stabilizing, thickening or colouring agent(s), binding agent(s), filling agent(s), lubricating agent(s), suspending agent(s), sweetener(s), flavouring agent(s), gelatinizer(s), anti-oxidant(s), preservative(s), pH regulator(s), wetting agent(s) or components normally found in corresponding products The composition of the invention comprises the HAmer of the invention and/or at least one factor capable of mobilizing stem cells in an amount sufficient to produce the desired effect. Other ingredients as well as other specific components of the pharmaceutical compositions may either be obtained commercially or prepared by conventional techniques known in the art. The compositions may be manufactured by any conventional processes known in the art.

The following examples illustrate the present invention. The examples are not to be construed to limit the claims in any manner whatsoever.

EXAMPLES

Materials and Methods

This section describes the materials and methods common to all examples 1 to 9.

Animal-model for Peripheral Blood Stem Cell Mobilization Studies

Adult (8-10 weeks) female, age-matched C57BL/6J (Jackson stock nr 000664, the Charles River Laboratories) CD45.2 mice were used in the in vivo mobilization experiments. The acclimatization period was always at least 7 days before the experiments. The animals were individually identified by ear and tail numbering and were housed in a Scantainer (Scanbur A/S, Karlslunde, Denmark) in Makrolon III cages. The animal room temperature was 21±2° C. and humidity was between 40-60%. Lightning was artificial, 12 h light and 12 h dark. The mice were provided with irradiated fodder and normal tap water ad libitum. Average weight of all animals in the experiments was 18.8±1.5 g. No formal randomization or grouping was done. Animals were randomly allocated to the study groups. All animals were weighed before the first dosing and in the end of each study.

Formulation of Test Items and Dosing

Sterile filtered PBS (pH 7.2) served as vehicle in all studies and was injected intravenously in the tail vein in similar volumes (50 or 100 µl) and time-points as the other test items within each study. Recombinant pegylated granulocyte-colony stimulatory factor (G-CSF), pegfilgrastim (Neulasta™, Amgen), with the stock concentration 10 mg/ml, was diluted immediately before the injections in sterile filtered PBS (pH 7.2) to yield a 0.25-0.5 mg/ml dosing solution. The animals obtained 25 µg pegfilgrastim (Neulasta™) subcutaneously at a dose volume of 50 or 100 µl on study day 0. The LMW hyaluronic acid derivatives HA and 6-O-S HA were prepared for injections into sterile filtered PBS in 5-10 mg/ml solutions and injected intravenously in the tail vein in dose volumes of 50 or 100 µl yielding 500 µg doses/mouse.

Experimental Protocol

The LMW hyaluronic acid (HA) derivatives were tested for capability to mobilize hematopoietic stem and progenitor cells to peripheral blood after 500 µg i.v. injections at the following time-points: 4h, 1d, 2d, 3d and 5d post-injections. Repetitive dosing was tested with daily 500 µg i.v. injections and sampling was done either on experimental days 2 (after 3 doses) or 5 (after 6 doses) after the first injection on day 0. Abnormal clinical signs or mortality was not observed with the LMW HA derivatives with 500 µg doses. The LMW HA derivatives were also tested in combination with a single dose of pegfilgrastim (Neulasta™). In combinatorial G-CSF+ LMW HA studies, pegfilgrastim was always injected s.c. at experimental day 0 and the LMW HA derivatives were administered i.v. as a) single doses of 500 µg at experimental day 3,
b) single doses of 500 µg 1 or 4 hours before sampling, or
c) as repetitive doses of 500 µg daily from experimental day 0-5 (in total 6 doses).

The vehicle groups were always injected with 0.9% NaCl by similar routes, volumes and time-points as the experimental groups.

Sampling and Sample Handling

Blood samples were drawn by cardiac puncture under isoflurane (4-4.5%) anesthesia using EDTA (K3)-rinsed syringe and needle. The blood samples were transferred from syringe into EDTA (K3) tubes (Venoject 3 ml) and they were stored at room temperature until further processing. After the bleeding, the animals were immediately euthanized. Spleens were collected in PBS (pH 7.2)-2 mM EDTA-0.1% bovine serum albumin buffer and stored at room temperature until weighing. Femurs were collected for bone marrow isolation when needed.

Cell Isolation and Differential Counts

The leukocyte, erythrocyte and platelet contents were determined for all blood samples by automated blood cell counter Sysmex XT-2000i by diluting the mouse blood 1:4 with 0.9% NaCl.

Mononuclear cells were isolated by carefully overlaying 3 ml Ficoll-Paque® (GE Healthcare) with peripheral blood diluted 1:2 in phosphate buffered saline (PBS)-2 mM EDTA. Tubes were centrifuged for 40 minutes at 400×g without brake. The mononuclear cell layer at the interphase was collected and washed twice in PBS-2 mM EDTA. Tubes were centrifuged for 10 minutes at 300×g. Mononuclear cell yields were counted using a Bürker chamber.

Bone marrow was isolated from femurs by making small incisions with scalpels and flushing out the marrow with 21G needle using Iscoves' MDM media (Invitrogen) supplemented with 2% FCS (Invitrogen).

Flow Cytometry

Flow cytometric analysis was performed on FACSAria (Becton Dickinson Biosciences) with a 488-nm argon laser for (PE, FITC and PE-Cy7), a 633-nm hene laser for (APC and APC-Cy7). Fluorescense was measured using 530/30-nm (FITC), 585/42-nm (PE), 780/60-nm (PE-Cy7), 660/20-nm (APC) and 780/60 (APC-Cy7) bandpass filters. Data visualization utilizing bi-exponential displays were analysed by FACSDiva software (BD Biociences).

Hematopoietic Cell Populations of Mouse Peripheral Blood by Flow Cytometric Analysis.

Peripheral mouse blood was diluted 1:5 in 0.9% NaCl (Baxter). Fluorescence labels (ebiosciences, except APC-CD45 BD Biosciences): 0.04 µg phycoerythrin (PE)-conjugated CD11c (dendritic cells; clone N418; cat#12-0114), fluorescein isothiocyanate (FITC)-conjugated 0.3 µg TER-119 (erythroid cells; clone TER-119; cat#11-5921), 0.1 allophycocyanin (APC)-conjugated CD314 (natural killer cells; clone CX5; 17-5882), 0.08 µg APC-Cyanine 7 (Cy7)-conjugated CD3e (T cells; clone 17A2; cat#27.0032) and 0.04 µg PE-Cy7 conjugated CD45R (B cells; RA3-6B2; 25-0452) were combined in one tube and 0.08 µg PE-conjugated CD115 (for monocytes and macrophages; clone AFS98; cat#12-1152), 0.2 µg FITC-conjugated-CD41 (megakaryocytes and hematopoietic progenitors; clone MWReg30; cat#11-0411), 0.08 µg APC-conjugated CD45 (leukocytes; clone 30-F11; cat#559864) and 0.03 µg PE-Cy7-conjugated LY-6G (neutrophils; clone RB6-8C5; cat#25-5931) were combined in another tube, incubated for 30 minutes on ice protected from light. To eliminate red blood cells, 2 ml of fresh 1×FACS lysing solution was added to the tube, mixed carefully, incubated for 10 minutes in dark at room temperature and centrifuged 300×g for 5 minutes. Cells were washed with 2 ml of buffer (phosphate buffered saline (PBS)-2 mM EDTA containing 0.3% of ultrapure bovine serum albumin), centrifuged 300×g for 5 minutes. Cells were resuspended in 200 µl of buffer and analyzed within 4 hours from the labelling.

The fluorescence labels were selected according to brightness and minimal potential spectral overlap. The brightest fluorochrome was given to the 'dim' antibodies and vice versa. Antibodies in each cocktail were selected to best differentiate between closely related cell populations. To validate multicolour reagent panel and avoid minimal compromising of the readout, both fidelity controls and fluorescence-minus-one controls were used. These controls were also used to check the gating of the detected cell population. Comp-Beads Compensation Particles anti-rat/hamster IgGκ were used to compensate the fluorescence (BD biosciences). Each tandem-label with different lot# was compensated separately, unity of the tandem-label confirmed and the proper compensation of the automated calculations controlled manually.

The proportions of monocyte-neutrophil-eosinophil (MNE) populations were gated from the CD45+ cells with high side scatter, thus not including lymphocytes. Hematopoietic progenitors in the lymphoid cell population expressing CD115 or CD41 were also calculated. The proportions of T cells, B cells, NK cells, proerythroblasts and dendritic cells were analyzed by first gating the lymphocyte population and detecting the fluorescence labelling of the adequate marker. In addition, CD314+ cells had to be negative for CD3e to be considered NK cells. Immature dendritic cells were CD11c+ but negative for T and B cell markers CD3e and CD45R, respectively.

SLAM Immunophenotyping

The enrichment of long-term repopulating (LTR) hematopoietic stem cells was detected with representation of SLAM markers. Mononuclear cells isolated by Ficoll gradient were labelled with APC-CD45 (cat# 559864; BD Pharmingen), PE-CD150 (cat# 12-1501-82; eBiosciences) and FITC-CD48 (cat# 557484; BD Pharmingen). CD45+ cells expressing CD150, but not CD48 cell surface markers were determined as a population highly enriched with LTR hematopoietic stem cells.

Hematopoietic Progenitor Cell Assay (CFU)

Myeloid hematopoietic progenitor cells were further enumerated by the colony forming unit (CFU/CFC) assay. Progenitor cells that are restricted in their lineage potential and that have limited self-renewal capability can be detected in colony-forming cell (CFC) assays using semisolid media such as methylcellulose, agar or collagen. Progenitors that read out in culture assays can either be multipotent, e.g. capable of generating progeny of multiple blood cell types, or restricted to one or two lineages, e.g. erythrocytes, granulocytes, monocyte/macrophages or platelets. This culture system supports the proliferation and differentiation of individual progenitor cells, termed colony-forming cells (CFCs), into discrete colonies containing recognizable progeny. CFCs are classified and enumerated based on morphologic recognition of mature cells within the colony. Mouse myeloid CFC assay MethoCult® M3434 "Complete Medium with Cytokines" (Stem Cell Technologies) containing 1% Methylcellulose, 15% Fetal Bovine Serum, 1% Bovine Serum Albumin, 10 µg/ml insulin, 200 µg/ml transferrin, 50 ng/ml recombinant SCF, 10 ng/ml recombinant IL-3, 10 ng/ml IL-6 and 3 U/ml recombinant EPO in Iscoves' MDM media (Invitrogen) was used according to the manufacturer's instructions with $1 \times 10^5$ mononuclear cells isolated by Ficoll density centrifugation. The cells were plated in duplicate onto sterile 35 mm petri dishes. CFU-GEMM (granulocyte-erythrocyte-macrophage-megakaryocyte colony-forming cells), CFU-GM (granulocyte-macrophage colony-forming cells), BFU-E (burst-forming unit-erythroid) and CFU-E (colony-forming unit-erythroid) were scored after 8-10 days. The results are presented as the total score of all identified colonies.

Statistical Analysis

Results are expressed as average ±SD except for the cell counts presented as scatter dot plots with means±SEM. Statistical differences were determined by either two-tailed unpaired t test or one-way analysis of variance with Bonferroni's Multiple Comparison post test. Values of p<0.05 were considered to be statistically significant. GraphPad Prism 5 was used for statistical analysis.

Example 1

Figure 1:
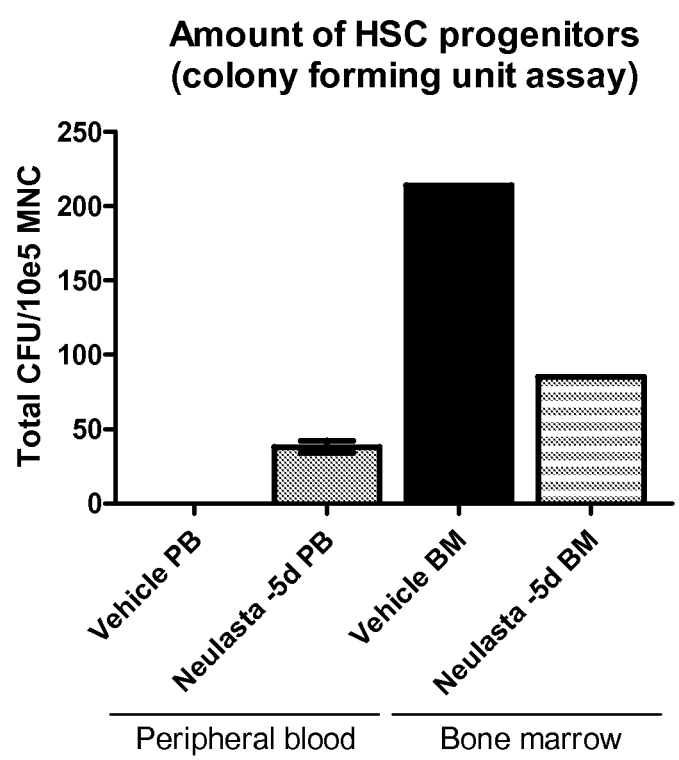
FIG. 1 shows the number of hematopoietic progenitor cells (HPCs) as determined by colony forming unit (CFU) assay. Peripheral blood and bone marrow mononuclear cells were isolated by Ficoll density centrifugation from vehicle C57B1/6J mice or C57B1/6J mice treated with 25 µg s.c. pegfilgrastim (Neulasta™) 5 days before sampling. $1 \times 10^5$ mononuclear cells were plated in duplicate and the total CFU amounts were counted 8-10 days after plating.

Determination of G-CSF Dose: Mobilization of HPC to Blood, HPC Contents in Bone Marrow and G-CSF-Induced Spleen Swelling To establish the dose of G-CSF control substance pegfilgrastim (Neulasta™, Amgen), the numbers of circulating hematopoietic progenitor cells (HPC) and HPCs in the bone marrow were determined by CFU assay in which $1 \times 10^5$ mononuclear cells isolated from both peripheral blood and bone marrow were used. The mice were treated with a single dose of 25 µg pegfilgrastim s.c. at day 0 and the samples were collected at day 5. As shown in FIG. 1, the number of circulating HPCs in mouse peripheral blood increased 40-50-fold over background with the dose and time-point used. The number of HPCs in the bone marrow decreased over 2-fold. The used pegfilgrastim dose did not leave the bone-marrow entirely devoid of HPCs, since there were still a higher number of HPCs left in the bone marrow/$1 \times 10^5$ bone marrow mononuclear cells than there were mobilized HPCc present in the blood after the G-CSF stimulation (FIG. 1). The levels of HPCs in untreated (vehicle) mice bone marrow were substantially higher than the HPC levels in the similar amount of mononuclear cells isolated from pegfilgrastim-mobilized peripheral blood (FIG. 1). The efficiency of 25 µg pegfilgrastim to mobilize HPCs was concluded to peak at 5 days after the s.c. injections as shown in FIG. 9A. Spleen swelling was evident already two days after the s.c. injection and, in line with the number of mobilized HPCs, also peaked 5 days after the injection (FIGS. 8A and 8B).

Example 2

LMW Hyaluronic Acid Oligosaccharide Derivatives Induce Alterations in Peripheral Blood Cell Profile Complete blood counts (numbers of white blood cells, mature red blood cells and platelets) of mouse peripheral blood were determined with automated blood cell counter.

Figure 2:
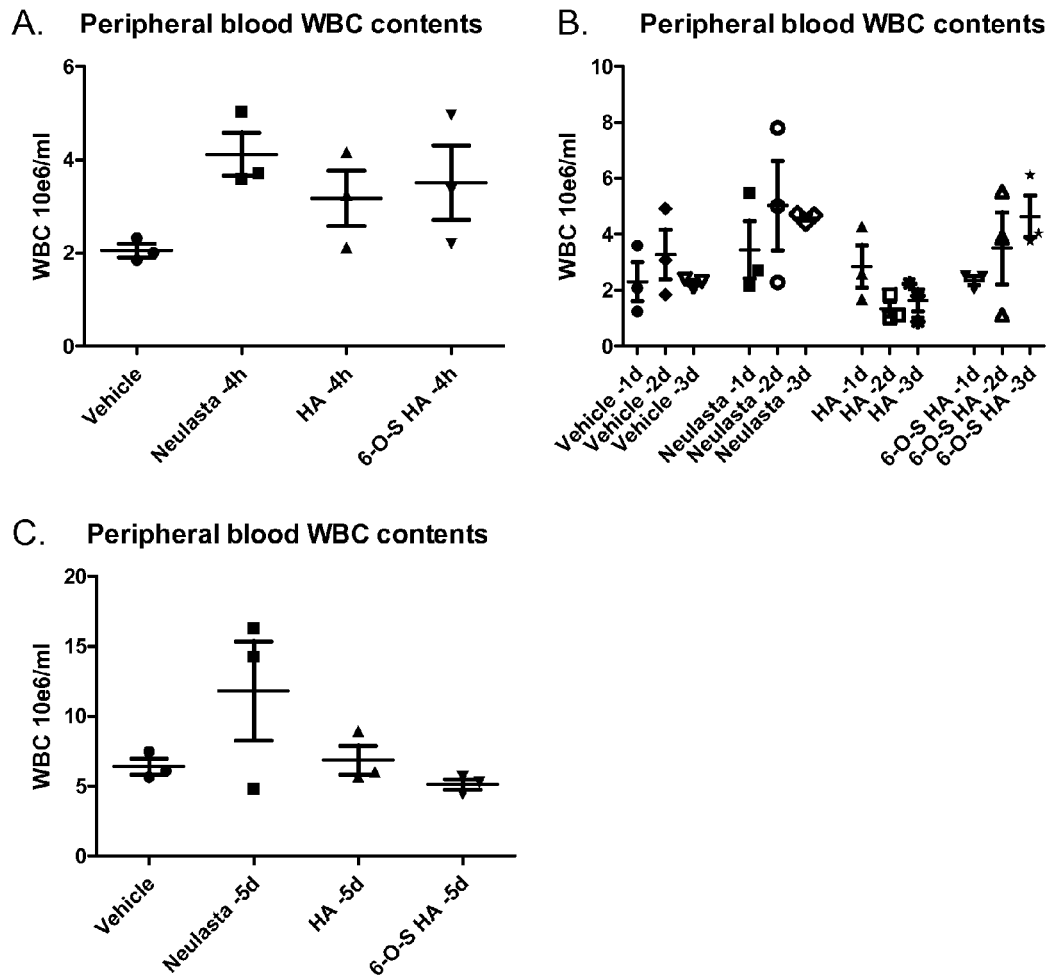
FIG. 2 shows the leukocyte (WBC) contents in mouse blood determined by automated blood cell counter Sysmex XT-2000i. Results are presented as scatter dot plots with means±SEM, with each point representing the value from a single mouse.

The white blood cell (WBC) contents in peripheral blood were studied after single dose administrations of 500 µg LMW hyaluronic acid derivatives HA and 6-O-S HA at different time-points and compared to WBC levels in the vehicle and pegfilgrastim (Neulasta™) groups. As shown in FIG. 2A, the LMW hyaluronic acid derivatives caused a rapid elevation in the numbers of circulating WBC 4 hours after i.v. injections and the levels were comparable to those caused by pegfilgrastim. After longer time-points (2-3 days after injections), the LMW 6-O-S HA caused an elevation in the WBC contents, especially 3 days after the i.v. injections (FIG. 1B), while the unsulphated LMW HA did not (FIG. 2B). 5 days after a 500 µg single dose administration of the LMW hyaluronic acid derivatives, the WBC counts were comparable to levels in control animals, although the WBC counts of pegfilgrastim injections remained high (FIG. 2C). Repetitive dosing (3 or 6 doses) of LMW unsulphated HA caused no evident alterations in WBC contents (FIG. 3A left panel). Three daily doses of LMW 6-O-S HA resulted in elevations in WBC contents, but the elevated WBC levels were slightly decreased by continued dosing for an additional three days (six doses together) of LMW 6-O-S HA (FIG. 3A right panel). In G-CSF combination therapy, a single s.c. injection of pegfilgrastim 5 days before sampling together with a single dose i.v. injection of LMW 6-O-S HA 4 hours or 1 hour before sampling did not change the G-CSF-alone-induced elevation of circulating WBC (FIG. 3B), but co-injections of a single dose of pegfilgrastim+unsulphated LMW HA might reduce the G-CSF-alone-induced WBC elevation 4 hours after the LMW HA injection (FIG. 3B, left panel). The results thus demonstrate that LMW hyaluronic acid derivatives can induce alterations in peripheral blood levels of WBC.

The red blood cell (RBC) and platelet (PLT) contents in peripheral blood were also studied in the same samples as was used for WBC determination. As presented in FIGS. 4 and 5, no evident changes in RBC levels were detectable after administration of the LMW HA derivatives. Pegfilgrastim was found to elevate the numbers of mature RBC 2-days after the s.c. injections (FIG. 4B and FIGS. 5A and 5B), but the RBC elevation was also occasionally seen to normalize back to control levels 5 days after the s.c. injection (FIG. 4C).

The PLT contents was generally unaltered after single dose (FIGS. 6B and 6C) and repetitive (FIG. 6A) administrations of the HA derivatives, but a dramatic decrease in circulating PLT contents was seen 4 hours after single injections of either the unsulphated LMW HA or the LMW 6-O-S HA (FIG. 6A). The levels were, however, normalized quickly back to the control levels (FIG. 6B and FIG. 6C) when longer time-points were studied after single dose administrations.

Pegfilgrastim is known to cause thrombocytopenia and this side effect was also evident in the used mouse model as demonstrated in FIGS. 6C, 7A right panel and 7B when 5 days had passed from the s.c. injection. Thrombocytopenia was not evident 1-3 days after the pegfilgrastim injection (FIG. 6B, FIG. 7A left panel). When mice were treated with the combination of pegfilgrastim and the LMW HA derivatives, the number of circulating platelets was not elevated (FIGS. 7A, B).

Example 3

LMW Hyaluronic Acid Oligosaccharide Derivatives do not Induce Spleen Swelling

As demonstrated in FIG. 8A, single or repetitive doses of the LMW hyaluronic acid derivatives did not cause any changes in spleen size at any time-points tested. Spleen swelling was evident for pegfilgrastim-treated mice already 3 days after the single s.c. injections (FIG. 8A, left panel) and the swelling was increased further during the next two days (FIG. 8A, middle and right panels). The combination of pegfilgrastim with i.v. injections of the LMW HA derivatives administered repeatedly (6 doses) did not increase the spleen swelling above the pegfilgrastim-alone-induced levels (FIG. 8B).

Example 4

Effects of LMW Hyaluronic Acid Oligosaccharides on Hematopoietic Progenitor Cell Mobilization In order to study effects of the LMW hyaluronic acid derivatives on mobilization of hematopoietic progenitor cells (HPCs), a colony-forming unit (CFU) assay was used. Peripheral blood was collected from mice after different time-points and injections schemes for the test substances. The number of HPCs was evaluated by plating similar amounts of isolated peripheral blood mononuclear cells. When the LMW hyaluronic acid derivatives were injected alone in 500 µg doses, either as single or repetitive injections, the number of circulating HPCs remained unaltered from vehicle levels (FIG. 9A). A single 25 µg s.c. injection of pegfilgrastim (Neulasta™) caused a robust mobilization of circulating HPCs, peaking at day 5 after the injection (FIG. 9A). When the unsulphated LMW hyaluronic acid derivative was administered in combination with a single s.c. injection of pegfilgrastim (Neulasta™), a statistically significant increase in HPC mobilization was not observed (FIG. 9B). The 6-O-S LMW HA, however, evidently synergized the HPC mobilization induced by pegfilgrastim alone (FIG. 9B). Clearly, G-CSF+ a single dose of 6-O-S LMW HA given only 1 hour before sample collection, substantially boosted G-CSF-induced HPC mobilization (FIG. 9B).

This time-point was chosen for further studies with larger animal groups (n=6). The synergistic effect of the 6-O-S sulphated LMW HA on G-CSF-induced mobilization of HPCs was statistically significant ($p<0.05$) as compared to the pegfilgrastim-alone group (FIG. 10A). The mean increase in the synergistic effect was approximately 70% (mean of Neulasta™-only group: 18.8 colonies/$10^5$ mononuclear cells, mean of Neulasta™+6-O-S HA −1 hour group: 31.5 colonies/$10^5$ mononuclear cells). Spleen swelling was slightly increased in the combination therapy group (FIG. 10B), but was not significantly increased compared to the Neulasta™-alone-induced spleen swelling (FIG. 10B). The minor increase seen in spleen swelling in the combination therapy group was probably only reflecting the increased HPC mobilization event, since we could not see any evidence for 6-O-S LMW HA-induced spleen swelling by itself (FIG. 8A).

Example 5

LMW Sulphated Hyaluronic Acid Oligosaccharides Synergizes with G-CSF to Mobilize Hematopoietic Progenitor Cells, but do not Further Increase the Amounts of Granulocytes The effect of the LMW 6-O-S HA on hematopoietic stem cell (HSCs) mobilization was studied by comparing the colony-forming unit (CFU) assay results, measuring circulating HPCs, to the immunophenotypic profile of circulating blood cells as determined by flow cytometry. G-CSF is known to mobilize HSCs undirectly by a protease-dependent pathway: G-CSF stimulate the bone marrow to produce granulocytes, and further to neutrophils. As a consequence, the release of a number of proteases is increased from both neutrophils, monocytes and unknown cell types, resulting in proteolytic cleavage of key adhesion molecules between the HSCs and the endosteal niche in the bone marrow.

In the used mouse model, G-CSF treatment induced a robust increase in the total number of circulating monocytes, neutrophils and eosinophils (MNEs) (FIG. 11A), which largely composed of granulocytes (FIG. 11B). However, a further increase in the levels of circulating MNEs as a pool or, more specifically, granulocytes was not found when giving combinatory dosing of both G-CSF 5 days before sampling +6-O-S LMW HA 1 hour before sampling (FIGS. 11A and 11B). The amounts of circulating HPCs were, however, seen to be elevated in the combination group (FIG. 10A). This indicates that the synergistic effect of G-CSF+ a single dose of sulphated LMW HA was through interactions between the LMW sulphated HA and adhesion molecules on HSCs and cognate ligands expressed in the endosteal niche in the bone marrow.

Example 6

LMW Sulphated Hyaluronic Acid Mobilize HSC with Long-Term Repopulating Capacity as Determined by SLAM Immunoprofile Although mobilization of HPCs may be of use for short-term repopulation in clinical settings, long-term repopulation and reconstitution of the hematopoietic cell system in a transplant recipient demands the presence of mobilized long-term repopulating hematopoietic stem cells (LTR-HSCs). Good markers for mouse LTR-HSCs are the signaling lymphocyte activation molecule (SLAM) receptors CD150. The presence of SLAM (CD150+CD48−CD45+) positive cells in mouse blood was determined by flow cytometry after vehicle, pegfilgrastim or pegfilgrastim +6-O-S LMW HA dosing. Samples were collected 1 hour after the i.v. 6-O-S LMW HA injection in the G-CSF+6-O-S LMW HA group. As presented in FIG. 14, the levels of circulating SLAM+ cells were dramatically increased in pegfilgrastim treated mice as compared to control (vehicle) mice levels. SLAM+ cells were also present when the animals received combination therapy with both pegfilgrastim and a single dose of 6-O-S LMW HA one hour before sampling. The analyzed cell population is encircled in insets A. and B. in FIG. 14.

Example 7

Combination Therapy with G-CSF and LMW Sulphated Hyaluronic Acid Induces FAST Changes in Peripheral Blood Cell Contents A more thorough analysis of the profile of released and circulating blood and immune cells was studied by immunophenotyping and flow cytometry using antibodies against known cell-type specific cell surface epitopes. Also, the colony forming-unit (CFU) assay is limited to cells in the myeloid lineage and do not allow the detection of lymphoid progenitors, which can be accomplished with this strategy. Mice received either the vehicle, 25 µg pegfilgrastim s.c. once 5 days before sample collection, or the combi-treatment of 25 µg pegfilgrastim at −5 days and a 500 µg single i.v. dose of 6-O-S LMW HA 1 hour before sample collection. The results of the immunophenotyping are presented in FIGS. 11-13. The levels of monocytes, neutrophils and eosinophils (MNEs) as a pool were dramatically increased after G-CSF treatment, but the combination of G-CSF+6-O-S LMW HA did not increase the amounts of MNEs further (FIG. 11A). Within the MNEs, the granulocytes were the main cell population which proliferated following the G-CSF stimulation (FIG. 11B). The G-CSF+6-O-S LMW HA combi treatment did not have a further effect on granulocyte proliferation (FIG. 11B). The levels of monocytes and macrophages as a pool decreased by the G-CSF stimulation and might further decrease when combining G-CSF with 6-O-S LMW HA (FIG. 11C).

The levels of CD45+CD115+ progenitors were increased by the G-CSF stimulation and a combination of G-CSF+6-O-S LMW HA made the increase of this progenitor pool statistically significant as compared to the levels in vehicle animals (FIG. 12A). The levels of CD45+CD41+ progenitors were decreased from control levels in both G-CSF and G-CSF+6-O-S LMW HA treatments (FIG. 12B). The levels of Ter-119+ proerythro-blasts were seen to decrease after G-CSF treatment, but the combination of G-CSF+6-O-S LMW HA could bring the proerythroblast levels back to control levels (FIG. 12C). In line with results from complete blood counts for platelet levels, more specific immunophenotyping with flow cytometry also revealed decreased levels of megakaryocytes and platelets after G-CSF stimulation and the levels were not altered by a combination of G-CSF+6-O-S LMW HA (FIG. 12D).

The levels of peripheral blood lymphocytes were increased due to G-CSF stimulation and combination with G-CSF+6-O-S LMW HA caused a statistically significant increase in the total levels of lymphocytes as compared to control (vehicle) levels (FIG. 13A). Within the lymphocyte population, the levels of CD3+ T-cells, NK (CD314+) cells, CD45R+ B-cells and lymphoid dendritic cells (CD11c+) were determined separately as presented in FIGS. 13 B-E. G-CSF and G-CSF+6-O-S LMW HA caused specific effects on the CD3+ T-cells, CD45R+ B-cells and lymphoid dendritic cell (CD11c+) levels, especially concerning the lymphoid dendritic cells where a combination of G-CSF+6-O-S LMW HA caused a significant increase in CD11c+ cells as compared to control levels (FIG. 13E). The NK cell levels remained unaltered (FIG. 13C).

Example 8

6-O-S LMW HA can Induce Proliferation of Erythrocyte Precursor Cells in G-CSF Treatments By analyzing Ter-119+ proerythroblastic cells in mouse peripheral blood by flow cytometry, a combination of G-CSF+6-O-S LMW HA could normalize the proerythroblast levels back to control levels when comparing to the decrease induced by G-CSF alone (FIG. 12C).

Example 9

Lymphocyte Profile

A more specific analysis of the immunophenotypic profile of circulating lymphocytes was analyzed with antibodies against CD3+ T-cell, NK (CD314+) cell, CD45R+ B-cell and lymphoid dendritic cell (CD11c+) and flow cytometry. The analysis was conducted on the gated lymphocyte population (FIG. 13A). A combination of G-CSF+6-O-S LMW HA could rapidly change the composition of specific lymphocytes in circulating blood as compared to the G-CSF-alone caused changes (FIGS. 13 B-E). It is especially noteworthy that a 6-O-S LMW HA boost lowered the amounts of G-CSF-alone-induced CD3+ T-cells increase (FIG. 13B), increased the levels of G-CSF-alone-induced CD45R B-cells decrease (FIG. 13D) and further increased the levels of lymphoid dendritic cells as compared to the G-CSF-alone levels (FIG. 13E). The composition of lymphoid cells is important in many clinical settings, for example in graft-versus-host disease.

Example 10

Hyaluronic Acid Preparates
Medium Molecular Weight Hyaluronic Acid by Acid Hydrolysis and Size Exclusion Chromatography Macromolecular hyaluronic acid sodium salt from *Streptococcus* sp. (Calbiochem, Cat. No. 385908) was treated by mild aqueous acid hydrolysis according to standard procedure in controlled reaction to prepare smaller molecular weight hyaluronic acid fragments. The product was purified and fractionated by size exclusion high performance liquid chromatography (HPLC) with preparative Supedex column (GE Healthcare) in aqueous ammonium bicarbonate buffer as shown in FIG. 15. Fractions (see Table 1) were evaporated to dryness, dissolved in water and analyzed by MALDI-TOF mass spectrometry according to standard procedure to determine their composition. The acid-hydrolyzed polymer fragments were shown to be $HexNAc_n HexA_n$ components (with disaccharide repeats). The GlcNAc deacetylation degree was between 7% and 10%.

The composition of the fractions selected for the pooled preparate are shown in Table 1. Thereafter, the pooled preparate was a mixture of polymers with 10-46 monomers (10 mer to 46 mer), peaking at 16 mer to 18 mer. By weight, 60% of the material was 10 mer to 18 mer, 24% was 20 mer to 28 mer, and 16% was 30 mer to 46 mer. By molecules, 75% of the material was 10 mer to 18 mer, 17% was 20 mer to 28 mer, and 8% was 30 mer to 46 mer. Relative proportions of smaller fragments were greater than those of larger fragments; for example, relative proportion of 10 mer fragments was over 10% of the preparate by weight, while relative proportion of 46 mer fragments was about 0.1% of the preparate by weight.

After pooling, the GlcA groups were changed into sodium salt by adding an equimolar amount of sodium salt solution and evaporating to dryness. For use, the preparate was dissolved in phosphate buffered saline (PBS) and sterile-filtered according to standard procedure. FIG. 2A shows the size exclusion HPLC chromatogram of the pooled preparate. The preparate was further analyzed by proton nuclear magnetic resonance spectroscopy (NMR) in $D_2O$ according to standard procedures and using internal acetone as reference. By proton NMR, the preparate was determined identical to hyaluronic acid. It was also determined that the preparate was essentially homogeneous with regard to its reducing and non-reducing ends: reducing end monosaccharide was GlcNAc and the non-reducing end monosaccharide was GlcA.

Commercial Medium Molecular Weight Hyaluronic Acid Preparate.

The size exclusion chromatogram of commercially obtained 4.8 kDa hyaluronic acid sodium salt from Lifecore Biomedical, Minnesota, USA (Lot GSP252-4) is shown in FIG. 16B. This product had nearly similar peak elution position than the acid hydrolyzed and fractionated product described above while it contained slightly more higher molecular weight components (FIG. 16A). By proton NMR, this product was similar to the previous preparate. By mass spectrometry, the GlcNAc deacetylation level was defined to be less than 2%, and the polymer preparate was shown to be a mixture of HexNAc$_n$HexA$_n$ and HexNAc$_n$HexA$_{n+1}$ components (mixture of components with either GlcNAc or GlcA as a terminal monosaccharide). For use, the preparate was dissolved in phosphate buffered saline (PBS) and sterile-filtered according to standard procedure.

TABLE 1

Composition of the pooled fractions from acid-hydrolyzed hyaluronic acid preparate

| Pooled fraction [1] | % by weight [2] | mol-% [3] | MALDI-TOF mass spectrometry results |
|---|---|---|---|
| 1 [4] | 2.8 | 1.2 | 32 mer to 46 mer, median = 38 mer |
| 2 | 3.0 | 1.4 | |
| 3 | 3.2 | 1.6 | |
| 4 | 3.3 | 1.8 | |
| 5 | 3.3 | 1.9 | |
| 6 | 3.4 | 2.1 | |
| 7 | 3.4 | 2.2 | 22 mer to 30 mer, median = 26 mer |
| 8 | 3.5 | 2.3 | |
| 9 | 3.5 | 2.5 | |
| 10 | 3.4 | 2.4 | |
| 11 | 3.4 | 2.9 | |
| 12 | 3.4 | 2.9 | 18 mer to 24 mer, median = 20 mer |
| 13 | 3.4 | 3.2 | |
| 14 | 3.3 | 3.1 | |
| 15 | 3.3 | 3.1 | |
| 16 | 3.3 | 3.1 | 16 mer to 20 mer |
| 17 | 3.2 | 3.4 | |
| 18 | 3.2 | 3.3 | |
| 19 | 3.1 | 3.3 | |
| 20 | 3.1 | 3.2 | |
| 21 | 3.1 | 3.7 | |
| 22 | 3.0 | 3.7 | 14 mer |
| 23 | 2.8 | 3.4 | |
| 24 | 2.6 | 3.2 | |
| 25 | 2.8 | 3.9 | |
| 26 | 3.0 | 4.2 | 12 mer |
| 27 | 2.7 | 3.8 | |
| 28 | 2.1 | 2.9 | |
| 29 | 2.1 | 3.5 | |
| 30 | 2.5 | 4.3 | |
| 31 | 3.0 | 5.0 | 10 mer |
| 32 | 2.6 | 4.4 | |
| 33 [5] | 1.8 | 3.1 | |

[1] Each fraction was 2 min/10 ml. See FIG. 1 for the chromatogram.
[2] By absorbance at 214 nm.
[3] Estimation based on composition by mass spectrometry and relative proportion by weight.
[4] Corresponds to 128-130 min in FIG. 15.
[5] Corresponds to 192-194 min in FIG. 15.

Example 11

Sulfated Hyaluronic Acid Preparates

Medium molecular weight hyaluronic acid preparates were subjected to chemical sulfation in controlled reaction and conditions where mainly primary 6-hydroxyl groups of the GlcNAc residues were modified. 6-specific sulfation reactions are known in the art. Sulfation degree and specificity was analyzed by proton NMR with internal acetone as reference. Signals at 4.35 ppm and 4.25 ppm corresponding to 6-O-sulfation were used for quantitation of 6-O-sulfation degree against known hyaluronic acid backbone signals. In different experiments, products with on average 40% or 70% 6-O-sulfation degree were obtained. Other sulfation types were not detected. FIG. 16C shows the gel permeation HPLC chromatogram of another preparate with 50% O-sulfation degree. This sulfated product had similar elution position as the non-sulfated starting material (FIG. 16B), indicating that the two products had similar Stokes radius in aqueous solution. For use, the preparate was dissolved in phosphate buffered saline (PBS) and sterile-filtered.

It will be obvious to a person skilled in the art that, as the technology advances, the inventive concept can be implemented in various ways. The invention and its embodiments are not limited to the examples described above but may vary within the scope of the claims.

What is claimed:

1. A sulphated hyaluronan oligomer or polymer (HAmer) having the general formula:

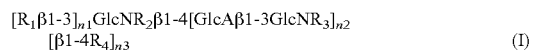

$$[R_1\beta 1\text{-}3]_{n1} GlcNR_2\beta 1\text{-}4[GlcA\beta 1\text{-}3GlcNR_3]_{n2}[\beta 1\text{-}4R_4]_{n3} \quad (I)$$

wherein;
$R_1$ is non-reducing group, which is GlcA or its beta-elimination product containing a double bond between 4- and 5-position of the uronic acid ring (delta-hexuroronic acid);
$R_2$ and $R_3$ are independently either H or acetyl or 3-10 C-alkyl or alkanoyl derivative of the amine or sulphate amide, the $R_3$ may also vary at each position of the chain;
$R_4$ is a reducing end group, which is GlcA or its reducing end derivative including preferably reducing (aldehyde containing) and non-reducing (aldehyde derivative) reducing end structures;
n1 and n3 are integers being either 0 or 1,
n2 is an integer varying from 2-50,
when n3 is 0 the reducing end GlcN may be derivatized as described for $R_4$;
the GlcN residue may be further derivatized by sulphate residue at position 2 or 4 or 6, and GlcA residue(s) may be optionally derivatized by sulphate residue at position 2 or 3, and
wherein at least 50% of sulphate residues of the HAmer are linked to the 6-position of the GlcN residue and having 0.1 to 1.5 sulphate residues per dimer as defined by variable n2 of Formula I.

2. The HAmer according to claim 1 wherein at least 70% of the sulphate residues of the HAmer are at the 6-position of the GlcNR-residues.

3. The HAmer according to claim 1 wherein at least 80% of the sulphate residues of the HAmer are at the 6-position of the GlcNR-residues.

4. The HAmer according to claim 1, wherein the HAmer comprises 0.1-1.0 sulphate residues per glycan backbone dimer defined by variable n2.

5. The HAmer according to claim 1, wherein the HAmer comprises at least 60% non-reducing end GlcA or derivative ($R_1$) and at least 60% reducing end GlcNR$_3$ or derivative.

6. The HAmer according to claim 1, wherein the HAmer comprises hexosamine with amine function, GlcN, between 0.1-20%.

7. The sulphated hyaluronan oligomer or polymer (HAmer) of claim 1 wherein n2 is an integer varying from 4-25.

8. A method of altering the relative amounts of blood cells or the types of blood cells of a subject, or for repairing the blood count of a subject, by administering to said subject a sulphated hyaluronan oligomer or polymer (HAmer) having the general formula:

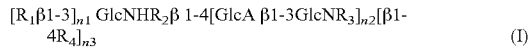

wherein;

R$_1$ is non-reducing group, which is GlcA or its beta-elimination product containing a double bond between 4- and 5-position of the uronic acid ring (delta-hexuronic acid);

R$_2$ and R$_3$ are independently either H or acetyl or 3-10 C-alkyl or alkanoyl derivative of the amine or sulphate amide, the R$_3$ may also vary at each position of the chain;

R$_4$ is a reducing end group, which is GlcA or its reducing end derivative including preferably reducing (aldehyde containing) and non-reducing (aldehyde derivative) reducing end structures;

n1 and n3 are integers being either 0 or 1, n2 is an integer varying from 2-50, when n3 is 0 the reducing end GlcN may be derivatized as described for R$_4$;

the GlcN residue may be further derivatized by sulphate residue at position 2 or 4 or 6, and GlcA residue(s) may be optionally derivatized by sulphate residue at position 2 or 3, and wherein at least 50% of sulphate residues of the HAmer are linked to the 6-position of the GlcN residue and having 0.1 to 1.5 sulphate residues per dimer as defined by variable n2 of Formula I.

9. The method of claim 8, wherein at least 70% of the sulphate residues of the HAmer are at the 6-position of the GlcNR-residues.

10. The method of claim 8, wherein at least 80% of the sulphate residues of the HAmer are at the 6-position of the GlcNR-residues.

11. The method of claim 8, wherein the HAmer comprises 0.1-1.0 sulphate residues per glycan backbone dimer defined by variable n2.

12. The method of claim 8, wherein the HAmer comprises at least 60% non-reducing end GlcA or derivative (R$_1$) and at least 60% reducing end GlcNR$_3$ or derivative.

13. The method of claim 8, wherein the HAmer comprises hexosamine with amine function, GlcN, between 0.1-20%.

14. The method of claim 8, wherein n2 is an integer varying from 4-25.

15. A pharmaceutical composition comprising at least one sulphated hyaluronan oligomer or polymer (HAmer) having the general formula:

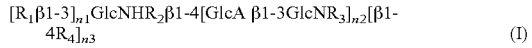

wherein;

R$_1$ is non-reducing group, which is GlcA or its beta-elimination product containing a double bond between 4- and 5-position of the uronic acid ring (delta-hexuronic acid);

R$_2$ and R$_3$ are independently either H or acetyl or 3-10 C-alkyl or alkanoyl derivative of the amine or sulphate amide, the R$_3$ may also vary at each position of the chain;

R$_4$ is a reducing end group, which is GlcA or its reducing end derivative including preferably reducing (aldehyde containing) and non-reducing (aldehyde derivative) reducing end structures;

n1 and n3 are integers being either 0 or 1, n2 is an integer varying from 2-50, when n3 is 0 the reducing end GlcN may be derivatized as described for R$_4$;

the GlcN residue may be further derivatized by sulphate residue at position 2 or 4 or 6, and GlcA residue(s) may be optionally derivatized by sulphate residue at position 2 or 3, and wherein at least 50% of sulphate residues of the HAmer are linked to the 6-position of the GlcN residue and having 0.1 to 1.5 sulphate residues per dimer as defined by variable n2 of Formula I.

16. The method of claim 15, wherein at least 70% of the sulphate residues of the HAmer are at the 6-position of the GlcNR-residues.

17. The method of claim 15, wherein at least 80% of the sulphate residues of the HAmer are at the 6-position of the GlcNR-residues.

18. The method of claim 15, wherein the HAmer comprises 0.1-1.0 sulphate residues per glycan backbone dimer defined by variable n2.

19. The method of claim 15, wherein the HAmer comprises at least 60% non-reducing end GlcA or derivative (R$_1$) and at least 60% reducing end GlcNR$_3$ or derivative.

20. The method of claim 15, wherein the HAmer comprises hexosamine with amine function, GlcN, between 0.1-20%.

21. The method of claim 15, wherein n2 is an integer varying from 4-25.

* * * * *